US011491106B2

(12) United States Patent
Chen et al.

(10) Patent No.: US 11,491,106 B2
(45) Date of Patent: Nov. 8, 2022

(54) ORAL SWEETENER COMPOSITIONS AND METHODS

(71) Applicant: The Coca-Cola Company, Atlanta, GA (US)

(72) Inventors: Youlung Chen, Marietta, GA (US); Xiaoliang Tan, Marietta, GA (US); Juvenal Higiro, Atlanta, GA (US); Indra Prakash, Alpharetta, GA (US); Robert M. Kriegel, Decatur, GA (US); Yu Shi, Marietta, GA (US); Haiyu Ren, Marietta, GA (US)

(73) Assignee: The Coca-Cola Company, Atlanta, GA (US)

( * ) Notice: Subject to any disclaimer, the term of this patent is extended or adjusted under 35 U.S.C. 154(b) by 0 days.

(21) Appl. No.: 16/625,063

(22) PCT Filed: Jun. 27, 2018

(86) PCT No.: PCT/US2018/039828
§ 371 (c)(1),
(2) Date: Dec. 20, 2019

(87) PCT Pub. No.: WO2019/006010
PCT Pub. Date: Jan. 3, 2019

(65) Prior Publication Data
US 2020/0163874 A1    May 28, 2020

Related U.S. Application Data

(60) Provisional application No. 62/525,579, filed on Jun. 27, 2017.

(51) Int. Cl.
| A61K 9/00 | (2006.01) |
| A23L 29/30 | (2016.01) |
| A23L 33/105 | (2016.01) |
| A23L 2/60 | (2006.01) |
| A61K 9/20 | (2006.01) |
| A61K 36/45 | (2006.01) |
| A61K 47/18 | (2017.01) |
| A61K 47/26 | (2006.01) |
| A61K 47/46 | (2006.01) |

(52) U.S. Cl.
CPC .............. *A61K 9/0056* (2013.01); *A23L 2/60* (2013.01); *A23L 29/30* (2016.08); *A23L 33/105* (2016.08); *A61K 9/006* (2013.01); *A61K 9/0095* (2013.01); *A61K 9/2018* (2013.01); *A61K 36/45* (2013.01); *A61K 47/183* (2013.01); *A61K 47/26* (2013.01); *A61K 47/46* (2013.01)

(58) Field of Classification Search
None
See application file for complete search history.

(56) References Cited

U.S. PATENT DOCUMENTS

| 3,681,087 A | 8/1972 | Johnson, Jr. |
| 3,898,323 A | 8/1975 | Fennell et al. |
| 4,031,260 A | 6/1977 | Westall et al. |
| 2002/0127190 A1 | 9/2002 | Zerbe et al. |
| 2011/0144218 A1 | 6/2011 | Posner et al. |
| 2016/0303149 A1 | 10/2016 | Lew |
| 2017/0119032 A1 | 5/2017 | Patron et al. |
| 2018/0133243 A1* | 5/2018 | Thompson ................ A61P 3/04 |

FOREIGN PATENT DOCUMENTS

| WO | WO 2007/107596 | 9/2007 |
| WO | WO 2013/032462 | 3/2013 |

OTHER PUBLICATIONS

European Search Report from EP Patent Application No. 18824114.0, dated Mar. 23, 2021.
International Search Report from PCT/US2018/039828, dated Nov. 5, 2018.

* cited by examiner

*Primary Examiner* — Nannette Holloman
(74) *Attorney, Agent, or Firm* — King & Spalding

(57) ABSTRACT

A single-use, oral dosage forms (e.g., fast-dissolving strips) is disclosed, as well as methods of using such oral dosage forms to sweeten edible compositions. Methods of manufacturing single-use, oral dosage forms are also provided.

18 Claims, 1 Drawing Sheet

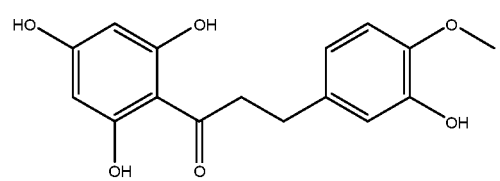
Hesperetin dihydrochalcone
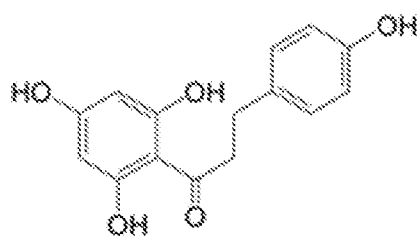
Phloretin
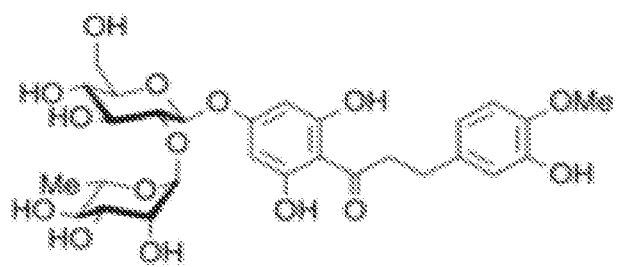
Neohesperidin dihydrochalcone (NHDC)

ORAL SWEETENER COMPOSITIONS AND METHODS

CROSS REFERENCE TO RELATED APPLICATIONS

This application is a national phase application under 35 U.S.C. § 371 of International Application No. PCT/US2018/039828, filed Jun. 27, 2018, which claims priority to U.S. Provisional Patent Application No. 62/525,579 filed Jun. 27, 2017. The contents of each of the above-identified applications is hereby fully incorporated herein by reference.

FIELD OF THE INVENTION

The present invention relates generally to single-use, oral dosage forms (e.g., fast-dissolving strips), as well as to methods of using such oral dosage forms to sweeten edible compositions. The present invention also relates to methods for manufacturing such oral dosage forms.

BACKGROUND OF THE INVENTION

Sugar (sucrose) has traditionally been used to sweeten edible products and many consumers prefer its taste. Yet, sugar is caloric and many consumers prefer to reduce their overall caloric intake while continuing to consume the edible products they enjoy.

High intensity sweeteners possess a sweetness level that is many times greater than the sweetness level of sugar. As a result, high intensity sweeteners can be used in smaller quantities than sugar to provide the same level of sweetness. Both synthetic and natural high intensity sweeteners are known and commonly used to sweetened edible products marketed as no or low-calorie, such as diet beverages.

While the human body requires carbohydrates to function properly (i.e., about 130 grams), many people consume far more carbohydrates than required—often from non-nutritive sources and disproportionately to protein.

There remains a need to provide compositions and methods that further reduce the carbohydrate content of edible products, while providing the same degree of sweetness enjoyed by consumers.

SUMMARY OF THE INVENTION

The present invention provides single-use, oral dosage forms suitable for use in sweetening edible compositions, as well as methods of using and manufacturing the same.

Advantageously, the oral dosage forms of the present invention permit a reduction in total carbohydrate intake compared to beverages conventionally sweetened with high intensity sweeteners, while providing equivalent or superior sweetness intensity. In a particular embodiment, the oral dosage form provides between about 5 to about 10 brix sweetness at a reduced concentration of carbohydrates compared to conventionally sweetened edible products. In one embodiment, concentration of carbohydrates is reduced by about 10%, about 15%, about 20%, about 25% or about 30% or more.

In a first aspect, the present invention provides a single-use, oral dosage form comprising miraculin and a dihydrochalcone derivative, wherein the oral dosage form fully dissolves within less than 60 seconds.

In one embodiment, the miraculin is purified. In another embodiment, the miraculin is provided as miraculin fruit powder. In still another embodiment, the miraculin is provided in miracle fruit pulp. In a particular embodiment, the amount of miraculin in the miraculin fruit powder is from about 0.01 to about 1 wt. %, or more particularly, about 0.05 wt. %.

In one embodiment, the oral dosage form further comprises at least one high intensity sweetener, at least one sweetness enhancer or combinations thereof. In a particular embodiment, the high intensity sweetener is natural. The purity of the natural high intensity sweetener may vary. In one embodiment, the natural high intensity sweetener has a purity of about from about 80% to about 100%, or more particularly, about 90% to about 100%, and even more particularly, about 95% or greater. In an exemplary embodiment, the natural high intensity sweetener is rebaudioside M, and more particularly, highly purity rebaudioside M. In another embodiment, the high intensity sweetener is synthetic. In an exemplary embodiment, the synthetic high intensity sweeter is aspartame.

In another embodiment, the oral dosage form further comprises one more excipients. In a particular embodiment, the excipients are selected from the group consisting of bulking agents, emulsifying agents, lubricants, flavors and sweeteners, gas producing disintegrants or superdisintigrents. In another embodiment, the excipients are selected from a water-soluble polymer, a plasticizer and a saliva-inducing agent.

In an exemplary embodiment, the oral dosage form is a fast-dissolving, single-use oral dosage comprising miraculin, a dihydrochalcone derivative, and at least one high intensity sweetener selected from rebaudioside M or aspartame and wherein the fast-dissolving single use oral dosage form is a film or tablet.

In one embodiment, the ratio of miraculin to dihydrochalcone(s) is from about 5:1 to about 200:1, or more particularly, from about 20:1 to about 40:1. In exemplary embodiments, the ratio of miraculin to dihydrochalcone(s) is from about 5:1 to about 100:1, from about 10:1 to about 60:1 or about 15:1 to about 40:1.

In another embodiment, the miraculin is provided as miracle fruit powder and the ratio of miracle fruit powder to dihydrochalcone(s) is from about 2000:1 to about 5:1, or more particularly about 5001:1 to about 10:1, from about 200:1 to about 20:1, or more particularly, from about 150:1 to about 50:1, or about 100:1 to about 20:1.

In a particular embodiment, the miraculin is provided as miracle fruit powder and the ratio of miracle fruit powder to dihydrochalcone(s) is about 500:1 or less, or more particularly, about 400:1, about 350:1, about 300:1, about 250:1, about 200:1, about 150:1, about 100:1, about 50:1 or about 25:1.

In a particular embodiment, the miraculin is provided as miracle fruit powder and the ratio of miracle fruit powder to dihydrochalcone(s) is about 10:1 or less, or more particularly, about 5:1, about 4:1, about 3:1 or about 2.1.

In yet another embodiment, miraculin is provided in the form of miracle fruit pulp and the ratio of miracle fruit pulp to the dihydrochalcone compound(s) is about 15000:1 to about 50:1, such as, for example, from about 5000:1 to about 100:1 or from about 2000:1 to about 500:1.

In a particular embodiment, the miraculin is provided in the form of miracle fruit pulp and the ratio of miracle fruit pulp to the dihydrochalcone compound(s) is about 200:1 or less, or more particularly, about 150:1, about 100:1, about 75:1 or about 50:1.

In a particular embodiment, the dihydrochalcone compound is selected from the group consisting of hesperetin dihydrochalcone, phloretin, neohesperidin dihydrochalcone and combinations thereof.

In a second aspect, the present invention provides a method for enhancing the sweetness of an edible product, comprising consuming the oral dosage form disclosed herein prior to consuming the edible product.

The time interval between consuming the oral dosage form and the edible product may vary. In one embodiment, the time interval is less than about 3 minutes, or more particularly, less than about 1 minute.

In a particular embodiment, the edible product further comprises one or more sweeteners, sweetness enhancers or combinations thereof.

In a particular embodiment, the oral dosage form provides between about 5 to about 10 brix sweetness at a reduced concentration of carbohydrates compared to edible products conventionally sweetened with high intensity sweeteners. In one embodiment, concentration of carbohydrates is reduced by about 10%, about 15%, about 20%, about 25% or about 30% or more.

In a particular embodiment, the edible product is a beverage or beverage product (e.g., a beverage syrup).

In an exemplary embodiment, the edible product is a reduced or no-calorie beverage.

In a fourth embodiment, the present invention provides a method of making the oral dosage forms disclosed herein.

In a particular embodiment, the oral dosage form is a fast-dissolving tablet made by a method selected from the group consisting of freeze drying (lyophilization), tablet molding, spray drying, sublimation, direct compression or nanonization.

In another particular embodiment, the oral dosage form is a fast-dissolving strip made by a method selected from the group consisting of solvent casting, hot melt extrusion, semi-solvent casting, solid dispersion extrusion and rolling.

BRIEF DESCRIPTION OF THE FIGURES

FIG. 1: Depicts the chemical structure of certain dihydrochalcone compounds, including hesperetin dihydrochalcone, phloretin and neohesperidin dihydrochalcone (NHDC).

DETAILED DESCRIPTION OF THE INVENTION

I. Definitions

As used herein, the term "carbohydrate" generally refers to aldehyde or ketone compounds substituted with multiple hydroxyl groups, of the general formula $(CH_2O)n$, wherein n is 3-30, as well as their oligomers and polymers.

As used herein, "conventionally sweetened" with reference to an edible product refers to an edible product sweetened with a carbohydrate sweetener, a high intensity sweetener or both, but other than as described herein.

As used herein, the term "disintegration time" is the time in which the integral oral film breaks down and is no longer recognized as an integral unit after being brought into contact with saliva, water, or similar solvent.

As used herein, the term "dosage form" refers to the form in which the dose is consumed by the subject. Dosage forms, for example, may be solid, liquid or gaseous.

As used herein, the term "dissolvable form" refers to any refers to any compositions that dissolve into a solution in the mouth. Such compositions, in one embodiment, may dissolve within about 60 seconds or less after placement in the mouth without any chewing.

As used herein, the term "fast-dissolving film" or "fast-dissolving strip" refers to thin oral films which get absorbed in the buccal cavity with the help of saliva, as hydrating agent without requirement of water and give their effect through pre-gastric absorption from mouth, pharynx and oesophagus as the saliva passes down into the stomach.

As used herein, the term "high purity" compound being present in a given mixture in an amount greater than about 95% by weight on a dry basis.

The term "isosweet," as used herein, refers to compositions that have equivalent sweetness. Generally, the sweetness of a given composition is typically measured with reference to a solution of sucrose. See "A Systematic Study of Concentration-Response Relationships of Sweeteners," G. E. DuBois, D. E. Walters, S. S. Schiffman, Z. S. Warwick, B. J. Booth, S. D. Pecore, K. Gibes, B. T. Carr, and L. M. Brands, in Sweeteners: Discovery, Molecular Design and Chemoreception, D. E. Walters, F. T. Orthoefer, and G. E. DuBois, Eds., American Chemical Society, Washington, D.C. (1991), pp 261-276.

As used herein, the terms "natural high intensity sweetener", "NHIS", "NHIS composition", and "natural high intensity sweetener composition" are synonymous and refer to any sweetener found in nature which may be in raw, extracted, purified, or any other form, singularly or in combination thereof and characteristically have a sweetness intensity greater than sucrose, fructose, or glucose, yet have fewer calories.

As used herein, the term "oral dosage form" refers to a dosage form that is intended to be consumed by mouth.

As used herein, the term "saliva stimulating agent" refers to an agent that increases the production of saliva in order to, for example, help dissolve an oral dosage form.

As used herein, the term "sucrose equivalence," refers to the sweetness of a composition compared to a sucrose reference. Typically, taste panelists are trained to detect sweetness of reference sucrose solutions containing between 1-15% sucrose (w/v). Other compositions are then tasted at a series of dilutions to determine the concentration of the composition is as sweet (i.e. isosweet) to a given percent sucrose reference.

As used herein, the term "sweetness enhancer" refers to a component or compositions capable of enhancing or intensifying the perception of sweet taste of sweetener compositions or sweetened compositions. Generally, the sweetness enhancer enhances or potentiates the sweet taste of sweeteners without providing any noticeable sweet taste itself, i.e., is present at or below its sweetness recognition threshold.

As used herein, the term "sweetness recognition threshold," is the lowest known concentration of a sweet compound that is perceivable by the human sense of taste.

As used herein, the term "steviol glycoside(s)" refers to a glycoside of steviol, including, but not limited to, naturally occurring steviol glycosides, e.g. steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside X, rebaudioside D, rebaudioside N, rebaudioside O, synthetic steviol glycosides, e.g. enzymatically glucosylated steviol glycosides and combinations thereof.

As used herein, the terms "synthetic high intensity sweetener", SHIS", SHIS composition", and synthetic high intensity sweetener composition" are synonymous and refer to any sweetener not found in nature and characteristically have a sweetness intensity greater than sucrose, fructose, or glucose, yet have less calories.

II. Compositions

The present invention provides an oral dosage form, e.g., a single-use oral dosage form, that modifies the taste, e.g., enhances the sweetness, of an edible composition. The oral dosage form contains miraculin or miraculin in combination with at least one dihydrochalcone compound, as discussed further below. Advantageously, the oral dosage form modulates the taste of the edible composition when consumed by the subject prior to the edible composition, e.g., increases the sweetness of the edible composition.

1. Oral Dosage Forms

The oral dosage form may vary and include, for example, a liquid drop or fast-dissolving delivery system. A fast-dissolving drug delivery system dissolves or disintegrates quickly in the oral cavity upon the contact with saliva, resulting in solution or suspension of the administered compound(s) (e.g., miraculin). In certain instances, the fast-dissolving delivery system is a lickable coating on a plastic backing, such as on a package.

In one embodiment, the oral dosage form is a dissolving or disintegrating tablet, such as a fast-dissolving or disintegrating tablet. FDTs (also known as orodispersible tablets) are solid unit dosage forms that dissolve or disintegrate in the mouth, typically within <60 seconds. (Bhowmik et al,. Journal of Chemical and Pharmaceutical Research, 2009, 1(1): 163-177). Ideally, a fast-dissolving tablet exhibits a rapid disintegration rate, sufficient hardness to resist destruction in the course of manufacture and storage, and low cost. In exemplary embodiments, the fast-dissolving tablet can be administered without water and/or chewing.

Fast-dissolving tablets typically contain several excipients. Representative, non-limiting excipients suitable for use in the fast-dissolving tablets of the present invention include bulking agents, emulsifying agents, lubricants, flavors and sweeteners, gas producing disintegrants and so-called superdisintegrants. (Kuldeep et al., Journal of Pharmaceutical Science and Technology 2010; 2 (10): 318-329). Representative, non-limiting superdistingrents include cross linked carboxymethylcellulose (croscarmellose), sodium starch glycolate (primogel, explotab), polyvinylpyrollidone (polyplasdone) etc, which provide instantaneous disintegration of tablet after putting on tongue.

In a particular embodiment, the fast-dissolving tablet dissolves within the mouth/oral cavity in less than about 3 minutes, less than about 2 minutes, less than about 70 seconds, less than about 65 seconds, less than about 60 seconds, less than about 55 seconds, less than about 50 seconds, less than about 45 seconds, less than about 40 seconds, less than about 35 seconds, less than about 30 seconds, less than about 25 seconds, or less than about 20 seconds.

Various techniques for forming fast dissolving tablets are discussed further below.

In another embodiment, the oral dosage form is a strip or film, such as a fast-dissolving strip or film (FDF). The strip or film is edible, including any type of conventional dissolving oral edible strip or film. The quick-dissolve strip may be of any shape, such as oblong, square, round, rectangular, etc. The quick-dissolve strip may also have a variety of sizes. The films are designed to dissolve upon contact with a wet surface, such as the tongue, within a few seconds, meaning the consumer can take the product without need for additional liquid. The fast-dissolving film typically has a surface area of about between about 1 and about 20 $cm^2$, or more particularly, about 1 and about 15 $cm^2$, about 5 and about 10 $cm^2$. In certain embodiments, the surface area of the dissolving firm is between about 1 and about 10 $cm^2$ or about 1, about 2, about 3, about 4, about 5, about 6, about 7, about 8, about 9 or about 10 $cm^{2t}$. The amount of the miraculin in the dosage form (or miraculin plus one or more dihydrochalcone compounds) may vary. In exemplary embodiments, the amount is from about 2% to about 50%, and more particularly, between about 5% and about 30%, and even more particularly between about 5% and about 15%.

The film may contain one or more excipients including a water-soluble polymer, a plasticizer, a surfactant, a sweeting agent, a saliva stimulating agent, a filler, a cooling agent, a colorant or a flavorant.

The oral disintegrating film or strip includes a water dissolving polymer which allows the dosage form to quickly hydrate by saliva, adhere to mucosa, and disintegrate quickly when placed on the tongue or oral cavity. The water-soluble polymer may be natural or synthetic. Exemplary natural water-soluble polymers include carbohydrates (e.g., pullulan, sodium alignate, malodextrin, sodium starch glyconate), proteins (e.g., gelatin) or resins. Exemplary synthetic water-soluble polymers include cellulose derivatives (e.g., carboxy methylcellulose, hydroxypropyl methylcellulose, hydroxyl ethylcellulose, hydroxyl propylcellulose), vinyl polymers (e.g., polyvinyl alcohol, polyvinylpyrrolidone) and acrylic polymers (Eudragit®).

In one embodiment, the film may contain hydroxypropylmethyl cellulose, hydroxyethyl cellulose, hydroxypropyl cellulose, hydroxyalkyl methyl cellulose, polyvinyl pyrrolidone, carboxymethyl cellulose, polyvinyl alcohol, sodium alginate, polyethylene glycol, xanthan gum, tragacanth gum, guar gum, pullulan, acacia gum, arabic gum, and combinations thereof.

The weight percentage of the water-soluble polymer in the dissolvable film may vary. In exemplary embodiments, is about 40 to about 70 wt. %, more particularly about 40 to about 50 wt. %, about 50 to about 60 wt. %, or about 60 to about 70 wt. %. In one embodiment, the weight percentage of the water soluble polymer is between about 60 and about 65 wt. %.

The plasticizer may vary but should be compatible with the water soluble polymer. Suitable plasticizers for use in the fast-dissolvable film of the present invention include, but are not limited to, glycerol, glycerin, polyethylene glycol (e.g., PEG-300, PEG-400), propylene glycol, citrate derivatives (e.g., triacetin) and phthalate derivatives (e.g., dibutyl phthalate).

The weight percentage of the plasticizer in the dissolvable film may vary. In exemplary embodiments, is about 0.2 to about 20 wt. %, or more particularly, about 0.5 to about 10 wt. %, or more particularly about 1 to about 5 wt. %.

In an exemplary embodiment, the water soluble polymer is a cellulose derivative and the plasticizer is selected from the group consisting of glycerol, polyethylene glycol and propylene glycol.

In another exemplary embodiment, the water soluble polymer is a vinyl polymer and the plasticizer is glycerol.

Suitable surfactants for use in the fast-dissolvable film of the present invention include, but are not limited to, sodium lauryl sulfate, Tween, benzalkonium chloride and polaxamer 407.

Suitable saliva stimulating agents include, but are not limited to, glucose, fructose, xylose, maltose, lactose, sucrose, aspartame, sodium saccharine, citric acid, malic acid, absorbic acid, succinic acid, adipic acid, fumaric acid, tartaric acid and lactic acid. The amount of the saliva simulating agent may vary. In one embodiment, the saliva stimulating agent is present at about 2 to about 6 wt. %.

Suitable cooling agents include, but are not limited to, monomethyl succinate, WS3, WS23 and Utracoll II.

Suitable stabilizing and thickening agents include, but are not limited to, natural gums like xanthan gum, locust bean gum, carragenan and cellulosic derivatives. In exemplary embodiments, the stabilizing agent or thickening agent is between about 0.5 to about 5 wt. %, or more particularly about 1 to about 3 wt. %, or about 3 to about 5 wt. %.

Suitable flavoring agents include, but are not limited to, synthetic flavor oils, essential oils, mints, sweet confectionary flavors and sour fruit flavors.

Suitable coloring agents include, but are not limited to, FD & C colors, EU colors, natural colors and custom Pantone-matched colors In one embodiment, a fast-dissolving film or strip comprises xanthan, locust bean gum, guar, gellan gum, sodium alginate, carrageenan, pullulan, pectin, glycerol, propylene glycol or combinations thereof.

In a particular embodiment, the fast dissolving film dissolves within the oral cavity in less than about 3 minutes, less than about 2 minutes, less than about 70 seconds, less than about 65 seconds, less than about 60 seconds, less than about 55 seconds, less than about 50 seconds, less than about 45 seconds, less than about 40 seconds, less than about 35 seconds, less than about 30 seconds, less than about 25 seconds, or less than about 20 seconds.

In a particular embodiment, the fast dissolving film dissolves within the oral cavity in a time frame between about 90 seconds and about 60 seconds, about 80 seconds and about 50 seconds, about 70 seconds and about 40 seconds or about 60 seconds and about 30 seconds.

In another particular embodiment, the fast dissolving film dissolves within the oral cavity in about 90 seconds, about 85 seconds, about 80 seconds, about 75 seconds, about 70 seconds, about 65 seconds, about 60 seconds, about 55 seconds, about 50 seconds, about 45 seconds, about 40 seconds, about 35 seconds, about 30 seconds, about 25 seconds, about 20 seconds, or about 15 seconds or less.

Representative, non-limiting formulations of dissolvable films are provided in the Examples, below.

Various techniques for forming fast dissolving films are discussed further below In a further embodiment, the oral dosage form is a fast-dissolving capsule.

In a particular embodiment, the fast dissolving capsule dissolves within the oral cavity in less than about 3 minutes, less than about 2 minutes, less than about 70 seconds, less than about 65 seconds, less than about 60 seconds, less than about 55 seconds, less than about 50 seconds, less than about 45 seconds, less than about 40 seconds, less than about 35 seconds, less than about 30 seconds, less than about 25 seconds, or less than about 20 seconds.

Various techniques for forming fast dissolving films are discussed further below 2. Miraculin The oral dosage form of the present invention comprises miraculin, which may be provided in purified form or as miraculin fruit powder.

Miraculin is a taste-modifying glycoprotein contained in fruit of the plant *Synsepalum dulcificum* (also known as *Richadella dulcifica*). Miraculin was identified in 1968 to be a functional ingredient of miracle fruit (Kurihara and Beidler, Science (1968) 161 (847), pp. 1241-1243). Common names for the miracle fruit plant and its very include miracle fruit, miracle berry, miraculous berry, sweet berry, and in West Africa, where the species originates, agbayun, taami, asaa, and ledidi. The miraculin protein is in itself very stable and can be stored in pure form or in solution for months (e.g. 6 months) without loss of function. (Gibbs et al., (1996). Sweet and taste-modifying proteins: A review. Nutrition Research, 16(9), 1619-1630).

Miraculin has an effect of modifying the perceived quality and intensity of tastes, e.g., changing the sourness of a food to sweetness, with the effect lasting from minutes to hours (Kurihara, Y. (1992). Characteristics of Antisweet Substances, Sweet Proteins, and Sweetness-Inducing Proteins. Critical Reviews in Food Science and Nutrition, 32(3), 231-252).

The monomer form of miraculin is flavorless at all pH as well as at high concentration; the dimer form elicits its taste-modifying activity at acidic pH; a tetrameric form is also reported as active. Psychophysical studies have shown that the type of acid affects the strength of the taste modifying effect of miraculin, where weak acids produce a more potent taste-modifying effect than do strong acids. (Brouwer et al., Nature 220, 373-374 (1968).

The complete amino acid sequence of the miraculin protein as been determined (Theerasilp et al., J Biol Chem. (1989) 264 (12), pp. 6655-6659). It is a single polypeptide with 191 amino acid residues. The calculated molecular weight based on the amino acid sequence and the carbohydrate content (13.9%) is 24,600. Asn-42 and Asn-186 are linked N-glycosidically to carbohydrate chains. High homology is found between the amino acid sequences of miraculin and soybean trypsin inhibitor.

The nucleotide sequence of the gene has also been determined (Masuda et al., Gene (1995) 161, pp. 175-177). The full-length cDNA sequence of the miraculin gene has been reported in Masuda et al., Gene (1995) 161, pp. 175-177.

In one embodiment, the present invention provides an oral dosage form comprising purified miraculin. In exemplary embodiments, miraculin can be extracted and purified from the miracle fruit plant (He et al, Food Chemistry, (2015), 181, p. 19-24). Alternatively, miraculin can be produced transgenically, for example, by transgenic production in plants. (Jin et al, Journal of the Korean Society for Applied Biological Chemistry (2013), 56, pp. 271-264). The particular plant may vary. Non-limiting examples include lettuce, tomatoes and strawberries.

In another embodiment, the present invention provides an oral dosage form comprising miraculin provided in the form of miracle fruit powder. Miracle fruit powder is a flowable powder produced from miracle fruit. The amount of miraculin in the miracle fruit powder may vary. In exemplary embodiments, micraculin constitutes about 0.05% of the miracle fruit powder.

In one embodiment, the oral dosage form contains miraculin in the form of a miracle fruit powder in amount from about 1 to about 10, such as, for example, about 3 to about 10, about 3 to about 7 or about 3 to about 5 wt. %.

In another embodiment, the oral dosage form contains miraculin in the form of a miracle fruit powder in amount from about 4 to about 8%, such as, for example, about 4 to about 6%.

In an exemplary embodiment, the oral dosage form contains miraculin in the form of a miracle fruit powder in an amount of about 1.0, about 1.5, about 2.0, about 2.5, about 3.0, about 3.5, about 4.0, about 4.5, about 5.0, about 5.5, about 6.0, about 6.5 about 7.0 about 7.5, about 8.0, about 8.5, about 9.0, about 9.5 or about 10 wt. %.

In another embodiment, miraculin is provided in purified form.

In yet another embodiment, miraculin is provided in the form of miracle fruit pulp.

3. Dihydrochalcone Compounds

The oral dosage form of the present invention comprises miraculin in combination with one or more dihydrochalcone compound.

Suitable, non-limiting dihydrochalcone compounds include the dihydrochalcone compound of Formula I:

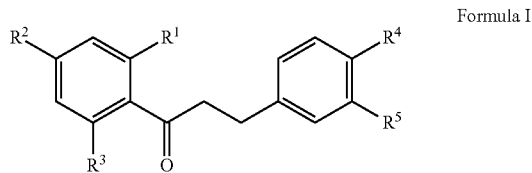

Formula I wherein $R^1$, $R^2$, $R^3$, $R^4$ and $R^5$ are each independently selected from H, OH, $OR^6$, alkyl and substituted alkyl, wherein $R^6$ is selected from alkyl, substituted alkyl and carbohydrate.

In one embodiment, the dihydrochalcone compound is selected from the group consisting of hesperetin dihydrochalcone (CC-00800), phloretin, neohesperidin dihydrochalcone, naringin dihydrochalcone and combinations thereof. The chemical formulas for several of these compounds are given in FIG. 1, hereto.

The weight percentage of the one or more dihydrochalcone compound(s) in the oral dosage form may vary. In one embodiment, the amount of the one or more dihydrochalcone compound(s) in the oral dosage form is from about 1 to about 5 wt. %, more particularly, from about 1 to about 4%, from about 1 to about 3%, or more particularly about 1.45% or about 3.0 wt. %.

In one embodiment, the amount of the one or more dihydrochalcone compound(s) in the oral dosage form is from about 1, about 1.2, about 1.4, about 1.6, about 1.8, about 2.0, about 2.2, about 2.4, about 2.6, about 2.8, about 3.0, about 3.2, about 3.4, about 3.6, about 3.8, about 4.0, about 4.2, about 4.4, about 4.6, about 4.8 or about 5.0 wt. %.

In another embodiment, the amount of the one or more dihydrochalcone compound(s) in the oral dosage form is less than about 5.0, less that about 4.5, less than about 4.0, less than about 3.5, less than about 3.0, less than about 2.5, less than about 2.0, less than about 1.5, less than about 1.0 or less than about 0.5 wt. %.

The weight ratio of the miraculin to the dihydrochalcone compound(s) may vary.

In a particular embodiment, the miraculin is provided in the form of miracle fruit powder and the ratio of miracle fruit powder to the dihydrochalcone compound(s) is about 2000:1 to about 5:1, such as, for example, from about 500:1 to about 10:1, from about 200:1 to about 20:1, from about 150:1 to about 50:1.

In another the miraculin is provided in the form of miracle fruit powder and the ratio of miracle fruit powder to the dihydrochalcone compound(s) is about 500:1 or less, or more particularly, about 400:1, about 350:1, about 300:1, about 250:1, about 200:1, about 150:1, about 100:1, about 75:1, about 50:1 or about 35:1.

In a particular embodiment, the miraculin is provided as miracle fruit powder and the ratio of miracle fruit powder to dihydrochalcone(s) is about 10:1 or less, such as for example, about 9:1, about 8:1, about 7:1, about 6:1, about 5:1, about 4:1, about 3:1, about 2:1 or about 1:1.

In another particular embodiment, the miraculin is provided as miracle fruit powder and the ratio of miracle fruit powder to dihydrochalcone(s) is about 10:1 or less, such as for example, about 9:1 to about 1:1, about 8:1 to about 2:1, about 7:1 to about 3:1 or about 6:1 to about 4:1.

In another embodiment, miraculin is provided in purified form and the ratio of miraculin to the dihydrochalcone compound is from about 5:1 to about 200:1, such as, for example, from about 5:1 to about 100:1, from about 10:1 to about 60:1 or about 15:1 to about 40:1. There is about 1-1.5 mg of miraculin per berry.

In yet another embodiment, miraculin is provided in the form of miracle fruit pulp and the ratio of miracle fruit pulp to the dihydrochalcone compound(s) is about 15000:1 to about 50:1, such as, for example, from about 5000:1 to about 100:1 or from about 2000:1 to about 500:1.

In a particular embodiment, the miraculin is provided in the form of miracle fruit pulp and the ratio of miracle fruit pulp to the dihydrochalcone compound(s) is about 200:1, or more particularly, about 150:1, about 100:1, about 75:1, about 100:1, about 75:1, about 50:1 or about 25:1.

4. Natural High Intensity Sweeteners

The oral dosage form of the present invention may optionally contain one or more natural high intensity sweeteners.

Advantageously, the amount of the natural high intensity sweetener present in the oral dosage form, or in the oral dosage form plus the edible product (e.g., beverage) with which it is used, is less than the amount of the natural high intensity sweetener used to conventionally sweeten a similar or the same edible product (e.g., beverage).

In one embodiment, the amount of natural sweetener present in the oral dosage form, or the oral dosage form plus the edible product (e.g., beverage) with which it is consumed, is more than about 10%, about 15%, about 20%, about 25% less than amount of the natural high intensity sweetener used to conventionally sweeten a similar or the same edible product (e.g., beverage).

In another embodiment, the amount of natural sweetener present in the oral dosage form, or the oral dosage form plus the edible product (e.g., beverage) with which it is consumed, is about 10% to about 15%, about 15% to about 25%, about 25% to about 35% or about 35% to about 40% less than amount of the natural high intensity sweetener used to conventionally sweeten a similar or the same edible product (e.g., beverage).

In another embodiment, the amount of natural sweetener present in the oral dosage form, or the oral dosage form plus the edible product (e.g., beverage) with which it is consumed, is about 5, about 10, about 15, about 20, about 25, about 30, about 35 or about 40% less than amount of the natural high intensity sweetener used to conventionally sweeten a similar or the same edible product (e.g., beverage).

Representative, non-limiting natural high intensity sweeteners suitable for use in the oral dosage form of the present invention include rebaudioside A, rebaudioside B, rebaudioside C, rebaudioside D, rebaudioside E, rebaudioside F, rebaudioside M, rebaudioside N, rebaudioside O, rebaudioside I, dulcoside A, dulcoside B, rubusoside, Stevia, stevioside, mogroside Me, mogroside IV, isomogroside V, mogroside V, mogroside VI, Luo Han Guo sweetener, siamenoside I, Siratose, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukuroziosidephlomisoside I, periandrin I, abrusoside A, cyclocarioside 1 or combinations thereof.

The purity of the natural high intensity sweetener may vary. In one embodiment, the natural high potency sweetener may be provided in the form of an extract at any purity percentage. When the natural high intensity sweetener is provided as a non-extract, the purity of the natural high intensity sweetener may range for example from about 25% to about 100%. According to other embodiments, the purity of the natural high intensity sweetener may range from about 50% to about 100%: from about 70% to about 100%; from about 80% to about 100%; from about 90% to about 100%; from about 95% to about 100%; from about 95% to about 99.5%; from about 96% to about 100%; from about 97% to about 100%; from about 98% to about 100%; and from about 99% to about 100%.

In a particular embodiment, the oral dosage form contains miraculin and rebaudioside M.

Recently, rebaudioside M (also referred to in the literature as rebaudioside X), (13-[2-O-β-D-glucopyranosyl-3-O-β-D-glucopyranosyl-β-D-glucopyranosyl)oxy] ent kaur-16-en-19-oic acid-[2-O-β-D-glucopyranosyl-3-O-β-D-glycopyranosyl) ester was isolated from *Stevia rebuadiana* and characterized:

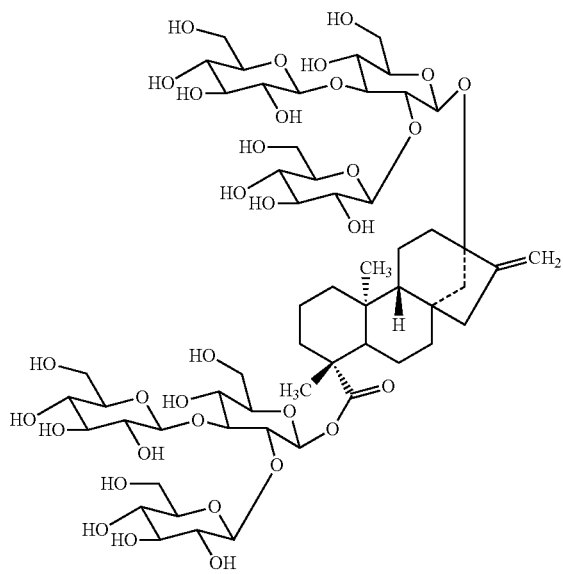

Rebaudioside M is present in minute quantities in *Stevia rebuadiana*, about 0.05-0.5% by weight. Methods of isolating rebaudioside X have been disclosed in PCT/US2012/070562, the contents of which are incorporated herein by reference. Reb M may be provided a pure compound or, alternatively, as part of an extract.

Rebaudioside M may be provided at a purity ranging from about 50% to about 100%; from about 70% to about 100%; from about 80% to about 100%; from about 90% to about 100%; from about 95% to about 100%; from about 95% to about 99.5%; about 96% to about 100%; from about 97% to about 100%; from about 98% to about 100%; and from about 99% to about 100%.

Rebaudioside M is also commercially available from Chromadex.

In an exemplary embodiment, the present invention provides an oral dosage form that contains (i) miraculin in the form of a miracle fruit powder in amount from about 3 to about 10% wt. % of the oral dosage form, and more particularly, about 5.5 wt. %; (ii) rebaudioside M in a wt. % of about 0.01 to about 0.1% of the oral dosage form and more particularly, about 0.035%; and (iii) phloretin in a wt. % of about 1 to about 5 wt. %, more particularly about 1 to about 3%, and even more particularly about 1.45%. In one embodiment, the oral dosage form, or the oral dosage form in combination with the edible product with which it is used, contains less rebaudioside M than an edible product (e.g., a beverage) conventionally sweetened with rebaudioside M, and more particularly, about 10% less, about 15% less, about 20% less, about 25% less, about 30% less, about 35% less, about 40% less, about 45% less, about 50% less, about 55% less, about 60% less, about 65% less, about 70% less or about 75% less (or greater) rebaudioside M than an edible product (e.g., a beverage) conventionally sweetened with rebaudioside M but maintains the equivalent or superior sweetness.

In another exemplary embodiment, the oral dosage form contains (i) miraculin in the form of a miracle fruit powder in amount from about 3 to about 10% wt. %, and more particularly, about 7.0 wt. % (ii) rebaudioside M in a wt. % of about 0.01 to about 0.1%, and more particularly, about 0.035% and (ii) phloretin in a wt. % of about 1 to about 5, and more particularly, about 1 to about 3, and even more particularly about 1.45%. In one embodiment, the oral dosage form, or the oral dosage form in combination with the edible product (e.g., beverage) with which it is used, contains less rebaudioside M than an edible product conventionally sweetened with rebaudioside M, and more particularly, about 10% less, about 15% less, about 20% less, about 25% less, about 30% less, about 35% less, about 40% less, about 45% less, about 50% less, about 55% less, about 60% less, about 65% less, about 70% less or about 75% less (or greater) reb M than a an edible product (e.g., beverage) conventionally sweetened with reb M but maintains the equivalent or superior sweetness.

In one embodiment, the oral dosage form contains miraculin and rebaudioside A.

Rebaudioside A is a high-potency diterpenoid glycoside sweetener having the chemical structure:

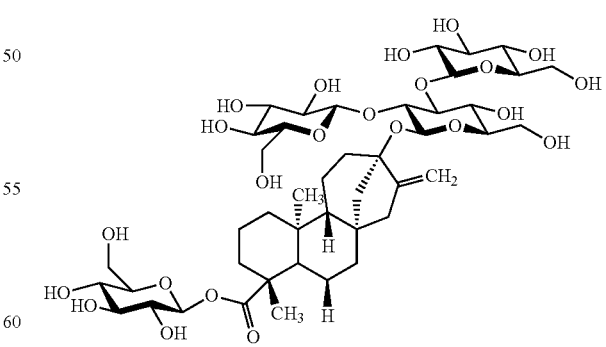

Rebaudioside A is isolated and extracted, along with other steviol glycosides, from the *Stevia rebaudiana* (Berton) plant ("*Stevia*"), which is commercially cultivated in Japan, Singapore, Taiwan, Malaysia, South Korea, China, Israel, India, Brazil, Australia, and Paraguay. It is a natural non-caloric sweetener with functional and sensory properties superior to those of many other non-caloric sweeteners. Processed forms of *Stevia* can be 70 to 400 times more potent than sugar; however, *Stevia* also has a bitter component. Of the four major diterpenoid glycoside sweeteners present in *Stevia*, rebaudioside A has been identified as the least astringent, the least bitter, and with the least persistent aftertaste. However, rebaudioside A still exhibits flavor and taste characteristics that distinguish it from sugar. Accordingly, it may be desirable to modify rebaudioside A to obtain novel compounds useful as sweetening compositions but exhibiting more desirable flavor and/or temporal profiles than rebaudioside A. The one or more natural high intensity sweeteners may optionally be included in the oral dosage form together with one or more synthetic high potency sweeteners, including those disclosed below.

Other aspects of the present invention provide an oral dosage form comprising miraculin and a high intensity sweetener. In one embodiment, this oral dosage form can be single-use. In another embodiment, this oral dosage form can fully dissolve within less than 60 seconds. The high intensity sweeteners can be any of the sweeteners described herein. In one embodiment, the sweetener can be rebaudioside A. Alternatively, the sweetener can be rebaudioside M.

In a particular embodiment, the ratio of miraculin to the high intensity sweetener compound(s) is about 500:1 or less; 450:1 or less, 425:1 or less, or 200:1 or less, or more particularly, about 150:1, about 100:1, about 75:1 or about 50:1. In one particular embodiment, the ratio of miraculin to the high intensity sweetener compound(s) is about 425:1 or less. In another embodiment, the ratio of miraculin to the high intensity sweetener compound(s) is about 150:1 or less.

In a particular embodiment, the miraculin is provided in the form of miracle fruit powder and the ratio of miracle fruit powder to the high intensity sweetener compound(s) is about 500:1 or less; 450:1 or less, 425:1 or less, or 200:1 or less, or more particularly, about 150:1, about 100:1, about 75:1 or about 50:1. In one particular embodiment, the ratio of miracle fruit powder to the high intensity sweetener compound(s) is about 425:1 or less. In another embodiment, the ratio of miracle fruit powder to the high intensity sweetener compound(s) is about 150:1 or less.

5. Synthetic High Intensity Sweeteners

The oral dosage form of the present invention may optionally contain one or more synthetic high intensity sweeteners.

Advantageously, the amount of the synthetic high intensity sweetener present in the oral dosage form, or in the oral dosage form plus the edible product (e.g., beverage) with which it is used, is less than the amount of the synthetic high intensity sweetener used to conventionally sweeten the edible product (e.g., beverage)

In one embodiment, the amount of synthetic high intensity sweetener present in the oral dosage form, or the oral dosage form plus the edible product with which it is used, is more than about 10%, about 15%, about 20%, about 25% less than amount of the synthetic high intensity sweetener used to conventionally sweeten beverages or more particularly, low or no-calorie beverages.

Representative, non-limiting examples of synthetic sweeteners suitable for use in the present invention sucralose, potassium acesulfame, aspartame, alitame, saccharin, neohesperidin dihydrochalcone, cyclamate, neotame, advantame, salts thereof, and the like.

In an exemplary embodiment, the oral dosage form contains (i) miraculin in the form of a miracle fruit powder in amount from about 3 to about 10% wt. %, and more particularly, about 5.5 wt. % (ii) aspartame in an amount from about 0.01 to about 0.1 wt. %, or more particularly, about 0.05 wt. %; and (iii) hesperetin dihydrochalcone in a weight percent of about 1 to about 5, more particularly about 1 to about 3 wt. %, and even more particularly about 3 wt. % or about 1.45 wt. %. In one embodiment, the oral dosage form, or the oral dosage form in combination with the edible product with which it is used, contains less aspartame than an edible product (e.g., beverage) conventionally sweetened with aspartame, and more particularly, about 10% less, about 15% less, about 20% less, about 25% less, about 30% less, about 35% less, about 40% less, about 45% less, about 50% less, about 55% less, about 60% less, about 65% less, about 70% less or about 75% less (or greater) aspartame than an edible product (e.g., beverage) conventionally sweetened with aspartame.

The one or more synthetic high intensity sweeteners may optionally be included in the oral dosage form together with one or more natural high potency sweeteners, including those disclosed above.

6. Sweet Taste Enhancing Compositions

The oral dosage form of the present invention may optionally contain one or more sweet taste enhancing compositions. The sweet taste enhancing compositions may be combined with any suitable sweetener to provide a sweetener composition having enhanced sweetness.

In particular embodiments, the at least one sweetness enhancer and at least one sweet taste improving composition may be the same. Thus, it is envisioned herein that the at least one sweetness enhancer may function both to enhance the sweetness of a sweetener while also modifying the temporal and/or flavor profile of a sweetener to be more sugar-like. In other particular embodiments, the at least one sweetness enhancer and at least one sweet taste improving composition may be different.

Representative, non-limiting examples of sweet taste enhancing compositions include carbohydrates, polyols, amino acids and their corresponding salts, polyamino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, polymers, other sweet taste improving taste additives imparting such sugar-like characteristics, and combinations thereof.

Advantageously, the amount of the sweet taste enhancing composition present in the oral dosage form, or in the oral dosage form plus the edible product with which it is used, is less than the amount of the sweet taste enhancing composition used to conventionally sweeten beverages.

In one embodiment, the amount of sweetness enhancer present in the oral dosage form, or the oral dosage form plus the edible product with which it is used, is more than about 10%, about 15%, about 20%, about 25% less than amount of the sweet taste enhancing composition used to conventionally sweeten beverages or more particularly, low or no-calorie beverages.

III. Edible Products

The oral dosage form of the present invention is suitable for use in sweetening or enhancing the sweetness of an edible product.

The edible product can be any edible or oral composition suitable for use in the mouth or ingestion. Exemplary edible products include, for example, pharmaceutical compositions, edible gel mixes and compositions, dental compositions, foodstuffs (confections, condiments, chewing gum, cereal compositions, baked goods, dairy products, and table-top sweetener compositions), beverages and beverage products.

The edible product can further contain one or more functional ingredients, detailed below. Functional ingredients include, but are not limited to, vitamins, minerals, antioxidants, preservatives, glucosamine, polyphenols and combinations thereof. Any suitable functional ingredient described herein can be used.

The edible product can further contain one or more additives including, but are not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, caffeine, flavorants and flavoring ingredients, astringent compounds, proteins or protein hydrolysates, surfactants, emulsifiers, weighing agents, juice, dairy, cereal and other plant extracts, flavonoids, alcohols, polymers and combinations thereof. Any suitable additive described herein can be used.

1. Beverages

In a particular embodiment, the edible product is a beverage.

As used herein, a "beverage" is a ready-to-drink beverage. Suitable ready-to-drink beverages include carbonated and non-carbonated beverages. Carbonated beverages include, but are not limited to, soft drinks, cola, lemon-lime flavored sparkling beverage, orange flavored sparkling beverage, grape flavored sparkling beverage, strawberry flavored sparkling beverage, pineapple flavored sparkling beverage, ginger-ale, soft drinks, root beer and malt beverages.

Non-carbonated beverages include, but are not limited to fruit juice, fruit-flavored juice, juice drinks, nectars, vegetable juice, vegetable-flavored juice, sports drinks, energy drinks, protein drinks, enhanced water with vitamins, near water drinks (e.g., water with natural or synthetic flavorants), coconut water, tea type (e.g. black tea, green tea, red tea, oolong tea), coffee, cocoa drink, beverage containing milk components (e.g. milk beverages, coffee containing milk components, café au lait, milk tea, fruit milk beverages), beverages containing cereal extracts, smoothies and combinations thereof.

Beverages contain a liquid matrix, i.e. the basic ingredient in which the ingredients are dissolved. In one embodiment, the liquid matrix is water of beverage quality, such as, for example deionized water, distilled water, reverse osmosis water, carbon-treated water, purified water, demineralized water and combinations thereof, can be used. Additional suitable liquid matrices include, but are not limited to phosphoric acid, phosphate buffer, citric acid, citrate buffer and carbon-treated water.

In one embodiment, the beverage contains inclusions, i.e. pulp, seed, chunks, etc.

Synthetic sweeteners may be present in the beverage in a concentration from about 0.3 ppm to about 3,500 ppm. Natural high potency sweeteners may be preset in the beverage in a concentration from about 0.1 ppm to about 3,000 ppm.

The beverage can further include additives including, but are not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, caffeine, flavorants and flavoring ingredients, astringent compounds, proteins or protein hydrolysates, surfactants, emulsifiers, weighing agents, juice, dairy, cereal and other plant extracts, flavonoids, alcohols, polymers and combinations thereof. Any suitable additive described herein can be used.

In one embodiment, the polyol can be present in the beverage in a concentration from about 100 ppm to about 250,000 ppm, such as, for example, from about 5,000 ppm to about 40,000 ppm.

In another embodiment, the amino acid can be present in the beverage in a concentration from about 10 ppm to about 50,000 ppm, such as, for example, from about 1,000 ppm to about 10,000 ppm, from about 2,500 ppm to about 5,000 ppm or from about 250 ppm to about 7,500 ppm.

In still another embodiment, the nucleotide can be present in the beverage in a concentration from about 5 ppm to about 1,000 ppm.

In yet another embodiment, the organic acid additive can be present in the beverage in a concentration from about 10 ppm to about 5,000 ppm.

In yet another embodiment, the inorganic acid additive can be present in the beverage in a concentration from about 25 ppm to about 25,000 ppm.

In still another embodiment, the bitter compound can be present in the beverage in a concentration from about 25 ppm to about 25,000 ppm.

In yet another embodiment, the flavorant can be present in the beverage a concentration from about 0.1 ppm to about 5,000 ppm.

In a still further embodiment, the polymer can be present in the beverage in a concentration from about 30 ppm to about 2,000 ppm.

In another embodiment, the protein hydrolysate can be present in the beverage in a concentration from about 200 ppm to about 50,000.

In yet another embodiment, the surfactant additive can be present in the beverage in a concentration from about 30 ppm to about 2,000 ppm.

In still another embodiment, the flavonoid additive can be present in the beverage a concentration from about 0.1 ppm to about 1,000 ppm.

In yet another embodiment, the alcohol additive can be present in the beverage in a concentration from about 625 ppm to about 10,000 ppm.

In a still further embodiment, the astringent additive can be present in the beverage in a concentration from about 10 ppm to about 5,000 ppm.

The beverage can further contain one or more functional ingredients, detailed below. Functional ingredients include, but are not limited to, vitamins, minerals, antioxidants, preservatives, glucosamine, polyphenols and combinations thereof. Any suitable functional ingredient described herein can be used.

It is contemplated that the pH of the beverage does not materially or adversely affect the sweetness enhancement. A non-limiting example of the pH range of the beverage may be from about 1.8 to about 10. A further example includes a pH range from about 2 to about 5. In a particular embodiment, the pH of beverage can be from about 2.5 to about 4.2. On of skill in the art will understand that the pH of the beverage can vary based on the type of beverage. Dairy beverages, for example, can have pHs greater than 4.2.

The titratable acidity of the beverage may, for example, range from about 0.01 to about 1.0% by weight of beverage.

In one embodiment, the sparkling beverage product has an acidity from about 0.01 to about 1.0% by weight of the beverage, such as, for example, from about 0.05% to about 0.25% by weight of beverage.

The carbonation of a sparkling beverage product has 0 to about 2% (w/w) of carbon dioxide or its equivalent, for example, from about 0.1 to about 1.0% (w/w).

The temperature of the beverage may, for example, range from about 4° C. to about 100° C., such as, for example, from about 4° C. to about 25° C.

The beverage can be a full-calorie beverage that has up to about 120 calories per 8 oz serving.

The beverage can be a mid-calorie beverage that has up to about 60 calories per 8 oz serving.

The beverage can be a low-calorie beverage that has up to about 40 calories per 8 oz serving.

The beverage can be a zero-calorie that has less than about 5 calories per 8 oz. serving.

In one embodiment, a reduced-calorie soda comprises, for example, caramel color.

2. Edible Gel Mixes and Edible Gel Compositions

In one embodiment, the edible product is an edible gel or edible gel mix.

Edible gels are gels that can be eaten. A gel is a colloidal system in which a network of particles spans the volume of a liquid medium. Although gels mainly are composed of liquids, and thus exhibit densities similar to liquids, gels have the structural coherence of solids due to the network of particles that spans the liquid medium. For this reason, gels generally appear to be solid, jelly-like materials. Gels can be used in a number of applications. For example, gels can be used in foods, paints, and adhesives.

Non-limiting examples of edible gel compositions for use in particular embodiments include gel desserts, puddings, jellies, pastes, trifles, aspics, marshmallows, gummy candies, or the like. Edible gel mixes generally are powdered or granular solids to which a fluid may be added to form an edible gel composition. Non-limiting examples of fluids for use in particular embodiments include water, dairy fluids, dairy analogue fluids, juices, alcohol, alcoholic beverages, and combinations thereof. Non-limiting examples of dairy fluids which may be used in particular embodiments include milk, cultured milk, cream, fluid whey, and mixtures thereof. Non-limiting examples of dairy analogue fluids which may be used in particular embodiments include, for example, soy milk and non-dairy coffee whitener. Because edible gel products found in the marketplace typically are sweetened with sucrose, it is desirable to sweeten edible gels with an alternative sweetener in order provide a low-calorie or non-calorie alternative.

3. Dental Compositions

In one embodiment, the edible product is a dental composition.

Dental compositions generally comprise an active dental substance and a base material. The dental composition may be in the form of any oral composition used in the oral cavity such as mouth freshening agents, gargling agents, mouth rinsing agents, toothpaste, tooth polish, dentifrices, mouth sprays, teeth-whitening agent, dental floss, and the like, for example.

4. Confections

In one embodiment, the edible product is a confection.

As referred to herein, "confection" can mean a sweet, a lollie, a confectionery, or similar term. The confection generally contains a base composition component and a sweetener component. The confection may be in the form of any food that is typically perceived to be rich in sugar or is typically sweet. According to particular embodiments of the present invention, the confections may be bakery products such as pastries; desserts such as yogurt, jellies, drinkable jellies, puddings, Bavarian cream, blancmange, cakes, brownies, mousse and the like, sweetened food products eaten at tea time or following meals; frozen foods; cold confections, e.g. types of ice cream such as ice cream, ice milk, lacto-ice and the like (food products in which sweeteners and various other types of raw materials are added to milk products, and the resulting mixture is agitated and frozen), and ice confections such as sherbets, dessert ices and the like (food products in which various other types of raw materials are added to a sugary liquid, and the resulting mixture is agitated and frozen); general confections, e.g., baked confections or steamed confections such as crackers, biscuits, buns with bean-jam filling, halvah, alfajor, and the like; rice cakes and snacks; table top products; general sugar confections such as chewing gum (e.g. including compositions which comprise a substantially water-insoluble, chewable gum base, such as chicle or substitutes thereof, including jetulong, guttakay rubber or certain comestible natural synthetic resins or waxes), hard candy, soft candy, mints, nougat candy, jelly beans, fudge, toffee, taffy, Swiss milk tablet, licorice candy, chocolates, gelatin candies, marshmallow, marzipan, divinity, cotton candy, and the like; sauces including fruit flavored sauces, chocolate sauces and the like; edible gels; crèmes including butter crèmes, flour pastes, whipped cream and the like; jams including strawberry jam, marmalade and the like; and breads including sweet breads and the like or other starch products, and combinations thereof 5. Condiment Compositions In one embodiment, the edible product is a condiment. Condiments, as used herein, are compositions used to enhance or improve the flavor of a food or beverage. Non-limiting examples of condiments include ketchup (catsup); mustard; barbecue sauce; butter; chili sauce; chutney; cocktail sauce; curry; dips; fish sauce; horseradish; hot sauce; jellies, jams, marmalades, or preserves; mayonnaise; peanut butter; relish; remoulade; salad dressings (e.g., oil and vinegar, Caesar, French, ranch, bleu cheese, Russian, Thousand Island, Italian, and balsamic vinaigrette), salsa; sauerkraut; soy sauce; steak sauce; syrups; tartar sauce; and Worcestershire sauce.

The condiment composition optionally may include other natural and/or synthetic high-potency sweeteners, bulk sweeteners, pH modifying agents (e.g., lactic acid, citric acid, phosphoric acid, hydrochloric acid, acetic acid, and combinations thereof), fillers, functional agents (e.g., pharmaceutical agents, nutrients, or components of a food or plant), flavorings, colorings, or combinations thereof.

6. Chewing Gum Compositions

In one embodiment, the edible product is a chewing gum composition.

Chewing gum compositions generally comprise a water-soluble portion and a water-insoluble chewable gum base portion. The water soluble portion dissipates with a portion of the flavoring agent over a period of time during chewing while the insoluble gum base portion is retained in the mouth. The insoluble gum base generally determines whether a gum is considered chewing gum, bubble gum, or a functional gum.

7. Cereal Compositions

In one embodiment, the edible product is a cereal composition.

Cereal compositions typically are eaten either as staple foods or as snacks. Non-limiting examples of cereal compositions for use in particular embodiments include ready-to-eat cereals as well as hot cereals. Ready-to-eat cereals are cereals which may be eaten without further processing (i.e. cooking) by the consumer. Examples of ready-to-eat cereals include breakfast cereals and snack bars. Breakfast cereals typically are processed to produce a shredded, flaky, puffy, or extruded form. Breakfast cereals generally are eaten cold and are often mixed with milk and/or fruit. Snack bars include, for example, energy bars, rice cakes, granola bars, and nutritional bars. Hot cereals generally are cooked, usually in either milk or water, before being eaten. Non-limiting examples of hot cereals include grits, porridge, polenta, rice, and rolled oats.

Cereal compositions generally comprise at least one cereal ingredient. As used herein, the term "cereal ingredient" denotes materials such as whole or part grains, whole or part seeds, and whole or part grass. Non-limiting examples of cereal ingredients for use in particular embodiments include maize, wheat, rice, barley, bran, bran endosperm, bulgur, sorghums, millets, oats, rye, triticale, buckwheat, fonio, *quinoa*, bean, soybean, amaranth, teff, spelt, and kaniwa.

8. Baked Goods

In one embodiment, the edible product is a baked good.

"Baked goods," as used herein, include ready to eat and all ready to bake products, flours, and mixes requiring preparation before serving. Non-limiting examples of baked goods include cakes, crackers, cookies, brownies, muffins, rolls, bagels, donuts, strudels, pastries, croissants, biscuits, bread, bread products, and buns.

Baked goods in accordance with particular embodiments of this invention generally comprise a combination of sweetener, water, and fat.

9. Dairy Products

In one embodiment, the edible product is a dairy product.

Dairy products and processes for making dairy products suitable for use in this invention are well known to those of ordinary skill in the art. Dairy products, as used herein, comprise milk or foodstuffs produced from milk. Non-limiting examples of dairy products suitable for use in embodiments of this invention include milk, milk cream, sour cream, crème fraiche, buttermilk, cultured buttermilk, milk powder, condensed milk, evaporated milk, butter, cheese, cottage cheese, cream cheese, yogurt, ice cream, frozen custard, frozen yogurt, gelato, vla, piima, filmjölk, kajmak, kephir, viili, kumiss, airag, ice milk, casein, ayran, lassi, khoa, or combinations thereof.

In particular embodiments of this invention, the processing of the dairy product from raw milk generally comprises the steps of pasteurizing, creaming, and homogenizing. Although raw milk may be consumed without pasteurization, it usually is pasteurized to destroy harmful microorganisms such as bacteria, viruses, protozoa, molds, and yeasts. Pasteurizing generally comprises heating the milk to a high temperature for a short period of time to substantially reduce the number of microorganisms, thereby reducing the risk of disease.

Particular embodiments of this invention comprise dairy products produced from milk by additional processing steps. As described above, cream may be skimmed from the top of milk or separated from the milk using machine-centrifuges. In a particular embodiment, the dairy product comprises sour cream, a dairy product rich in fats that is obtained by fermenting cream using a bacterial culture. The bacteria produce lactic acid during fermentation, which sours and thickens the cream. In another particular embodiment, the dairy product comprises crème fraiche, a heavy cream slightly soured with bacterial culture in a similar manner to sour cream. Crème fraiche ordinarily is not as thick or as sour as sour cream. In yet another particular embodiment, the dairy product comprises cultured buttermilk. Cultured buttermilk is obtained by adding bacteria to milk. The resulting fermentation, in which the bacterial culture turns lactose into lactic acid, gives cultured buttermilk a sour taste. Although it is produced in a different manner, cultured buttermilk generally is similar to traditional buttermilk, which is a by-product of butter manufacture.

According to other particular embodiments of this invention, the dairy products comprise milk powder, condensed milk, evaporated milk, or combinations thereof. Milk powder, condensed milk, and evaporated milk generally are produced by removing water from milk. In a particular embodiment, the dairy product comprises a milk powder comprising dried milk solids with a low moisture content. In another particular embodiment, the dairy product comprises condensed milk. Condensed milk generally comprises milk with a reduced water content and added sweetener, yielding a thick, sweet product with a long shelf-life. In yet another particular embodiment, the dairy product comprises evaporated milk. Evaporated milk generally comprises fresh, homogenized milk from which about 60% of the water has been removed, that has been chilled, fortified with additives such as vitamins and stabilizers, packaged, and finally sterilized. According to another particular embodiment of this invention, the dairy product comprises a dry creamer and a steviol glycoside blend of the present invention or a sweetener composition comprising the same.

In another particular embodiment, the dairy product provided herein comprises butter. Butter generally is made by churning fresh or fermented cream or milk. Butter generally comprises butterfat surrounding small droplets comprising mostly water and milk proteins. The churning process damages the membranes surrounding the microscopic globules of butterfat, allowing the milk fats to conjoin and to separate from the other parts of the cream. In yet another particular embodiment, the dairy product comprises buttermilk, which is the sour-tasting liquid remaining after producing butter from full-cream milk by the churning process.

In still another particular embodiment, the dairy product comprises cheese, a solid foodstuff produced by curdling milk using a combination of rennet or rennet substitutes and acidification. Rennet, a natural complex of enzymes produced in mammalian stomachs to digest milk, is used in cheese-making to curdle the milk, causing it to separate into solids known as curds and liquids known as whey. Generally, rennet is obtained from the stomachs of young ruminants, such as calves; however, alternative sources of rennet include some plants, microbial organisms, and genetically modified bacteria, fungus, or yeast. In addition, milk may be coagulated by adding acid, such as citric acid. Generally, a combination of rennet and/or acidification is used to curdle the milk. After separating the milk into curds and whey, some cheeses are made by simply draining, salting, and packaging the curds. For most cheeses, however, more processing is needed. Many different methods may be used to produce the hundreds of available varieties of cheese. Processing methods include heating the cheese, cutting it into small cubes to drain, salting, stretching, cheddaring, washing, molding, aging, and ripening. Some cheeses, such as the blue cheeses, have additional bacteria or molds introduced to them before or during aging, imparting flavor and aroma to the finished product. Cottage cheese is a cheese curd product with a mild flavor that is drained but not pressed so that some whey remains. The curd is usually washed to remove acidity. Cream cheese is a soft, mild-tasting, white cheese with a high fat content that is produced by adding cream to milk and then curdling to form a rich curd. Alternatively, cream cheese can be made from skim milk with cream added to the curd. It should be understood that cheese, as used herein, comprises all solid foodstuff produced by the curdling milk.

In another particular embodiment of this invention, the dairy product comprises yogurt. Yogurt generally is produced by the bacterial fermentation of milk. The fermentation of lactose produces lactic acid, which acts on proteins in milk to give the yogurt a gel-like texture and tartness. In particularly desirable embodiments, the yogurt may be sweetened with a sweetener and/or flavored. Non-limiting examples of flavorings include, but are not limited to, fruits (e.g., peach, strawberry, banana), vanilla, and chocolate. Yogurt, as used herein, also includes yogurt varieties with different consistencies and viscosities, such as dahi, dadih or dadiah, labneh or labaneh, bulgarian, kefir, and matsoni. In another particular embodiment, the dairy product comprises a yogurt-based beverage, also known as drinkable yogurt or a yogurt smoothie. In particularly desirable embodiments, the yogurt-based beverage may comprise sweeteners, flavorings, other ingredients, or combinations thereof.

Other dairy products beyond those described herein may be used in particular embodiments of this invention. Such dairy products are well known to those of ordinary skill in the art, non-limiting examples of which include milk, milk and juice, coffee, tea, vla, piima, filmjolk, kajmak, kephir, viili, kumiss, airag, ice milk, casein, ayran, lassi, and khoa.

According to particular embodiments of this invention, the dairy compositions also may comprise other additives. Non-limiting examples of suitable additives include sweeteners and flavorants such as chocolate, strawberry, and banana. Particular embodiments of the dairy compositions provided herein also may comprise additional nutritional supplements such as vitamins (e.g., vitamin D) and minerals (e.g., calcium) to improve the nutritional composition of the milk.

10. Tabletop Sweetener Compositions

In one embodiment, the edible product is a tabletop sweetener.

The tabletop sweetener can further include at least one bulking agent, additive, anti-caking agent, functional ingredient or combination thereof.

Suitable "bulking agents" include, but are not limited to, maltodextrin (10 DE, 18 DE, or 5 DE), corn syrup solids (20 or 36 DE), sucrose, fructose, glucose, invert sugar, sorbitol, xylose, ribulose, mannose, xylitol, mannitol, galactitol, erythritol, maltitol, lactitol, isomalt, maltose, tagatose, lactose, inulin, glycerol, propylene glycol, polyols, polydextrose, fructooligosaccharides, cellulose and cellulose derivatives, and the like, and mixtures thereof. Additionally, in accordance with still other embodiments of the invention, granulated sugar (sucrose) or other caloric sweeteners such as crystalline fructose, other carbohydrates, or sugar alcohol can be used as a bulking agent due to their provision of good content uniformity without the addition of significant calories.

As used herein, the phrase "anti-caking agent" and "flow agent" refer to any composition which assists in content uniformity and uniform dissolution. In accordance with particular embodiments, non-limiting examples of anti-caking agents include cream of tartar, calcium silicate, silicon dioxide, microcrystalline cellulose (Avicel, FMC BioPolymer, Philadelphia, Pa.), and tricalcium phosphate. In one embodiment, the anti-caking agents are present in the tabletop sweetener composition in an amount from about 0.001 to about 3% by weight of the tabletop sweetener composition.

The tabletop sweetener compositions can be packaged in any form known in the art. Non-limiting forms include, but are not limited to, powder form, granular form, packets, tablets, sachets, pellets, cubes, solids, and liquids.

In one embodiment, the tabletop sweetener composition is a single-serving (portion control) packet comprising a dry-blend. Dry-blend formulations generally may comprise powder or granules. Although the tabletop sweetener composition may be in a packet of any size, an illustrative non-limiting example of conventional portion control tabletop sweetener packets are approximately 2.5 by 1.5 inches and hold approximately 1 gram of a sweetener composition having a sweetness equivalent to 2 teaspoons of granulated sugar (~8 g). In a particular embodiment, a dry-blend tabletop sweetener formulation may contain a sweetener an amount from about 1% (w/w) to about 10% (w/w).

Solid tabletop sweetener embodiments include cubes and tablets. A non-limiting example of conventional cubes are equivalent in size to a standard cube of granulated sugar, which is approximately 2.2×2.2×2.2 $cm^3$ and weigh approximately 8 g. In one embodiment, a solid tabletop sweetener is in the form of a tablet or any other form known to those skilled in the art.

A tabletop sweetener composition also may be embodied in the form of a liquid, wherein a steviol glycoside blend of the present invention or a sweetener composition comprising the same is combined with a liquid carrier. Suitable non-limiting examples of carrier agents for liquid tabletop sweeteners include water, alcohol, polyol, glycerin base or citric acid base dissolved in water, and mixtures thereof. The sweetness equivalent of a tabletop sweetener composition for any of the forms described herein or known in the art may be varied to obtain a desired sweetness profile. For example, a tabletop sweetener composition may comprise a sweetness comparable to that of an equivalent amount of standard sugar. In another embodiment, the tabletop sweetener composition may comprise a sweetness of up to 100 times that of an equivalent amount of sugar. In another embodiment, the tabletop sweetener composition may comprise a sweetness of up to 90 times, 80 times, 70 times, 60 times, 50 times, 40 times, 30 times, 20 times, 10 times, 9 times, 8 times, 7 times, 6 times, 5 times, 4 times, 3 times, and 2 times that of an equivalent amount of sugar.

The edible products of the present invention may optionally include additional additives, detailed herein below. In some embodiments, the edible products contains additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, emulsifiers, weighing agents, gums, colorants, flavonoids, alcohols, polymers, essential oils, anti-fungal agents and combinations thereof. In some embodiments, the additives act to improve the temporal and flavor profile of the sweetener(s) to provide a taste similar to sucrose.

Suitable amino acid additives include, but are not limited to, aspartic acid, arginine, glycine, glutamic acid, proline, threonine, theanine, cysteine, cystine, alanine, valine, tyrosine, leucine, arabinose, trans-4-hydroxyproline, isoleucine, asparagine, serine, lysine, histidine, ornithine, methionine, carnitine, aminobutyric acid ($\alpha$-, $\beta$-, and/or $\delta$-isomers), glutamine, hydroxyproline, taurine, norvaline, sarcosine, and their salt forms such as sodium or potassium salts or acid salts. The amino acid additives also may be in the D- or L-configuration and in the mono-, di-, or tri-form of the same or different amino acids. Additionally, the amino acids may be α-, β-, γ- and/or δ-isomers if appropriate. Combinations of the foregoing amino acids and their corresponding salts (e.g., sodium, potassium, calcium, magnesium salts or other alkali or alkaline earth metal salts thereof, or acid salts) also are suitable additives in some embodiments. The amino acids may be natural or synthetic. The amino acids also may be modified. Modified amino acids refers to any amino acid wherein at least one atom has been added, removed, substituted, or combinations thereof (e.g., N-alkyl amino acid, N-acyl amino acid, or N-methyl amino acid). Non-limiting examples of modified amino acids include amino acid derivatives such as trimethyl glycine, N-methyl-glycine, and N-methyl-alanine. As used herein, modified amino acids encompass both modified and unmodified amino acids. As used herein, amino acids also encompass both peptides and polypeptides (e.g., dipeptides, tripeptides, tetrapeptides, and pentapeptides) such as glutathione and L-alanyl-L-glutamine. Suitable polyamino acid additives include poly-L-aspartic acid, poly-L-lysine (e.g., poly-L-α-lysine or poly-L-ε-lysine), poly-L-ornithine (e.g., poly-L-□α-ornithine or poly-L-□ε-ornithine), poly-L-arginine, other polymeric forms of amino acids, and salt forms thereof (e.g., calcium, potassium, sodium, or magnesium salts such as L-glutamic acid mono sodium salt). The poly-amino acid additives also may be in the D- or L-configuration. Additionally, the poly-amino acids may be α-, β-, γ-, δ-, and ε-isomers if appropriate. Combinations of the foregoing poly-amino acids and their corresponding salts (e.g., sodium, potassium, calcium, magnesium salts or other alkali or alkaline earth metal salts thereof or acid salts) also are suitable additives in some embodiments. The poly-amino acids described herein also may comprise co-polymers of different amino acids. The poly-amino acids may be natural or synthetic. The poly-amino acids also may be modified, such that at least one atom has been added, removed, substituted, or combinations thereof (e.g., N-alkyl poly-amino acid or N-acyl poly-amino acid). As used herein, poly-amino acids encompass both modified and unmodified poly-amino acids. For example, modified poly-amino acids include, but are not limited to, poly-amino acids of various molecular weights (MW), such as poly-L-α-lysine with a MW of 1,500, MW of 6,000, MW of 25,200, MW of 63,000, MW of 83,000, or MW of 300,000.

In particular embodiments, the amino acid is present in an amount effective to provide a concentration from about 10 ppm to about 50,000 ppm when present in an edible product, such as, for example, a beverage. In another embodiment, the amino acid is present in in an amount effective to provide a concentration from about 1,000 ppm to about 10,000 ppm when present in an edible product, such as, for example, from about 2,500 ppm to about 5,000 ppm or from about 250 ppm to about 7,500 ppm.

Suitable sugar acid additives include, but are not limited to, aldonic, uronic, aldaric, alginic, gluconic, glucuronic, glucaric, galactaric, galacturonic, and salts thereof (e.g., sodium, potassium, calcium, magnesium salts or other physiologically acceptable salts), and combinations thereof.

Suitable nucleotide additives include, but are not limited to, inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, alkali or alkaline earth metal salts thereof, and combinations thereof. The nucleotides described herein also may comprise nucleotide-related additives, such as nucleosides or nucleic acid bases (e.g., guanine, cytosine, adenine, thymine, uracil).

The nucleotide is present in an amount effective to provide a concentration from about 5 ppm to about 1,000 ppm when present in an edible product, such as, for example, a beverage.

Suitable organic acid additives include any compound which comprises a —COOH moiety, such as, for example, C2-C30 carboxylic acids, substituted hydroxyl C2-C30 carboxylic acids, butyric acid (ethyl esters), substituted butyric acid (ethyl esters), benzoic acid, substituted benzoic acids (e.g., 2,4-dihydroxybenzoic acid, 3-hydroxybenzoic acid, 3,4,5-trihydroxybenzoic acid), substituted cinnamic acids, hydroxyacids, substituted hydroxybenzoic acids, anisic acid substituted cyclohexyl carboxylic acids, tannic acid, aconitic acid, lactic acid, tartaric acid, citric acid, isocitric acid, gluconic acid, glucoheptonic acids, adipic acid, hydroxycitric acid, malic acid, fruitaric acid (a blend of malic, fumaric, and tartaric acids), fumaric acid, maleic acid, succinic acid, chlorogenic acid, salicylic acid, creatine, caffeic acid, bile acids, acetic acid, ascorbic acid, alginic acid, erythorbic acid, polyglutamic acid, glucono delta lactone, and their alkali or alkaline earth metal salt derivatives thereof. In addition, the organic acid additives also may be in either the D- or L-configuration.

Suitable organic acid additive salts include, but are not limited to, sodium, calcium, potassium, and magnesium salts of all organic acids, such as salts of citric acid, malic acid, tartaric acid, fumaric acid, lactic acid (e.g., sodium lactate), alginic acid (e.g., sodium alginate), ascorbic acid (e.g., sodium ascorbate), benzoic acid (e.g., sodium benzoate or potassium benzoate), sorbic acid and adipic acid. The examples of the organic acid additives described optionally may be substituted with at least one group chosen from hydrogen, alkyl, alkenyl, alkynyl, halo, haloalkyl, carboxyl, acyl, acyloxy, amino, amido, carboxyl derivatives, alkylamino, dialkylamino, arylamino, alkoxy, aryloxy, nitro, cyano, sulfo, thiol, imine, sulfonyl, sulfenyl, sulfinyl, sulfamyl, carboxalkoxy, carboxamido, phosphonyl, phosphinyl, phosphoryl, phosphino, thioester, thioether, anhydride, oximino, hydrazino, carbamyl, phosphor or phosphonato. In particular embodiments, the organic acid additive is present in an amount from about 10 ppm to about 5,000 ppm when present in an edible product, such as, for example, a beverage.

Suitable inorganic acid additives include, but are not limited to, phosphoric acid, phosphorous acid, polyphosphoric acid, hydrochloric acid, sulfuric acid, carbonic acid, sodium dihydrogen phosphate, and alkali or alkaline earth metal salts thereof (e.g., inositol hexaphosphate Mg/Ca).

The inorganic acid additive is present in an amount effective to provide a concentration from about 25 ppm to about 25,000 ppm when present in an edible product, such as, for example, a beverage.

Suitable bitter compound additives include, but are not limited to, caffeine, quinine, urea, bitter orange oil, naringin, quassia, and salts thereof.

The bitter compound is present in an amount effective to provide a concentration from about 25 ppm to about 25,000 ppm when present in an edible product, such as, for example, a beverage.

Suitable flavorant and flavoring ingredient additives for include, but are not limited to, vanillin, vanilla extract, mango extract, cinnamon, citrus, coconut, ginger, viridiflorol, almond, menthol (including menthol without mint), grape skin extract, and grape seed extract. "Flavorant" and "flavoring ingredient" are synonymous and can include natural or synthetic substances or combinations thereof. Flavorants also include any other substance which imparts flavor and may include natural or non-natural (synthetic) substances which are safe for human or animals when used in a generally accepted range. Non-limiting examples of proprietary flavorants include Döhler™ Natural Flavoring Sweetness Enhancer K14323 (Döhler™ Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™, Freehold, N.J., U.S.A.), and Sucramask™ (Creative Research Management, Stockton, Calif., U.S.A.).

The flavorant is present in an amount effective to provide a concentration from about 0.1 ppm to about 5,000 ppm when present in an edible product, such as, for example, a beverage.

Suitable polymer additives include, but are not limited to, chitosan, pectin, pectic, pectinic, polyuronic, polygalacturonic acid, starch, food hydrocolloid or crude extracts thereof (e.g., gum acacia senegal (Fibergum™), gum acacia seyal, carageenan), poly-L-lysine (e.g., poly-L-α-lysine or poly-L-ε-lysine), poly-L-ornithine (e.g., poly-L-α-ornithine or poly-L-ε-ornithine), polypropylene glycol, polyethylene glycol, poly(ethylene glycol methyl ether), polyarginine, polyaspartic acid, polyglutamic acid, polyethylene imine, alginic acid, sodium alginate, propylene glycol alginate, and sodium polyethyleneglycolalginate, sodium hexametaphosphate and its salts, and other cationic polymers and anionic polymers.

The polymer is present in an amount effective to provide a concentration from about 30 ppm to about 2,000 ppm when present in an edible product, such as, for example, a beverage.

Suitable protein or protein hydrolysate additives include, but are not limited to, bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, asparagine, glutamine, arginine, valine, isoleucine, leucine, norvaline, methionine, proline, tyrosine, hydroxyproline, and the like), collagen (e.g., gelatin), partially hydrolyzed collagen (e.g., hydrolyzed fish collagen), and collagen hydrolysates (e.g., porcine collagen hydrolysate).

The protein hydrosylate is present in an amount effective to provide a concentration from about 200 ppm to about 50,000 ppm when present in an dibble product, such as, for example, a beverage.

Suitable flavonoid additives are classified as flavonols, flavones, flavanones, flavan-3-ols, isoflavones, or anthocyanidins. Non-limiting examples of flavonoid additives include, but are not limited to, catechins (e.g., green tea extracts such as Polyphenon™ 60, Polyphenon™ 30, and Polyphenon™ 25 (Mitsui Norin Co., Ltd., Japan), polyphenols, rutins (e.g., enzyme modified rutin Sanmelin™ AO (San-fi Gen F.F.I., Inc., Osaka, Japan)), neohesperidin, naringin, neohesperidin dihydrochalcone, and the like.

The flavonoid additive is present in an amount effective to provide a concentration from about 0.1 ppm to about 1,000 ppm when present in an edible product, such as, for example, a beverage.

Suitable colorants include, but are not limited to, caramel color, natural colors such as Annatto, cochineal, betanin, turmeric, paprika, saffron, lycopene, elderberry juice, pandan, yellow No. 6, yellow No. 5, red No. 40, Green No. 3 and blue No. 1.

Suitable alcohol additives include, but are not limited to, ethanol. In particular embodiments, the alcohol additive is present in the an amount effective to provide a concentration from about 625 ppm to about 10,000 ppm when present in an edible product, such as, for example, a beverage.

Suitable astringent compound additives include, but are not limited to, tannic acid, europium chloride ($EuCl_3$), gadolinium chloride ($GdCl_3$), terbium chloride ($TbCl_3$), alum, tannic acid, and polyphenols (e.g., tea polyphenols). The astringent additive is present in an amount effective to provide a concentration from about 10 ppm to about 5,000 ppm when present in an edible product, such as, for example, a beverage.

Suitable essential oils include, but are not limited to, mustard oil, bitter orange and sweet orange, menthe *arvensis*, peppermint, cedarwood, lemon, *Eucalyptus globulus, Litsea cubeba*, clove and spearmint.

Suitable anti-fungal agents include, but are not limited to, Natamycin, amphotericin, anidulafungin, caspofungin, fluconazole, itraconazole, micafungin, posaconazole, voriconazole, and flucytosine.

Other additives include typical beverages additives, i.e. glycerol ester of wood rosin, coconut oil, brominated vegetable oil, carob bean gum, sucrose acetate isobutyrate, modified food starch, zinc gluconate and vitamin A palmitate.

Exemplary consumables include, but are not limited to edible gel mixes and compositions, dental compositions, foodstuffs (confections, condiments, chewing gum, cereal compositions, baked goods, dairy products, and tabletop sweetener compositions) beverages and beverage products.

The edible product can also contain one or more functional ingredients, which provide a real or perceived heath benefit to the product. Functional ingredients include, but are not limited to, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

Antioxidant

In certain embodiments, the functional ingredient is at least one antioxidant. Generally, according to particular embodiments of this invention, the at least one antioxidant is present in the edible product, e.g. beverage, in an amount sufficient to promote health and wellness.

As used herein "antioxidant" refers to any substance which inhibits, suppresses, or reduces oxidative damage to cells and biomolecules. Without being bound by theory, it is believed that antioxidants inhibit, suppress, or reduce oxidative damage to cells or biomolecules by stabilizing free radicals before they can cause harmful reactions. As such, antioxidants may prevent or postpone the onset of some degenerative diseases.

Examples of suitable antioxidants for embodiments of this invention include, but are not limited to, vitamins, vitamin cofactors, minerals, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavonoid phenolics, isothiocyanates, and combinations thereof. In some embodiments, the antioxidant is vitamin A, vitamin C, vitamin E, ubiquinone, mineral selenium, manganese, melatonin, α-carotene, β-carotene, lycopene, lutein, zeanthin, crypoxanthin, reservatol, eugenol, quercetin, catechin, gossypol, hesperetin, curcumin, ferulic acid, thymol, hydroxytyrosol, turmeric, thyme, olive oil, lipoic acid, glutathinone, gutamine, oxalic acid, tocopherol-derived compounds, butylated hydroxyanisole (BHA), butylated hydroxytoluene (BHT), ethylenediaminetetraacetic acid (EDTA), tert-butylhydroquinone, acetic acid, pectin, tocotrienol, tocopherol, coenzyme Q10, zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms (ECGC) theaflavin and its gallate forms, thearubigins, isoflavone phytoestrogens, genistein, daidzein, glycitein, anythocyanins, cyaniding, delphinidin, malvidin, pelargonidin, peonidin, petunidin, ellagic acid, gallic acid, salicylic acid, rosmarinic acid, cinnamic acid and its derivatives (e.g., ferulic acid), chlorogenic acid, chicoric acid, gallotannins, ellagitannins, anthoxanthins, betacyanins and other plant pigments, silymarin, citric acid, lignan, antinutrients, bilirubin, uric acid, R-α-lipoic acid, N-acetylcysteine, emblicanin, apple extract, apple skin extract (applephenon), rooibos extract red, rooibos extract, green, hawthorn berry extract, red raspberry extract, green coffee antioxidant (GCA), *aronia* extract 20%, grape seed extract (VinOseed), cocoa extract, hops extract, mangosteen extract, mangosteen hull extract, cranberry extract, pomegranate extract, pomegranate hull extract, pomegranate seed extract, hawthorn berry extract, pomella pomegranate extract, cinnamon bark extract, grape skin extract, bilberry extract, pine bark extract, pycnogenol, elderberry extract, mulberry root extract, wolfberry (gogi) extract, blackberry extract, blueberry extract, blueberry leaf extract, raspberry extract, turmeric extract, citrus bioflavonoids, black currant, ginger, acai powder, green coffee bean extract, green tea extract, and phytic acid, or combinations thereof. In alternate embodiments, the antioxidant is a synthetic antioxidant such as butylated hydroxytolune or butylated hydroxyanisole, for example. Other sources of suitable antioxidants for embodiments of this invention include, but are not limited to, fruits, vegetables, tea, cocoa, chocolate, spices, herbs, rice, organ meats from livestock, yeast, whole grains, or cereal grains.

Particular antioxidants belong to the class of phytonutrients called polyphenols (also known as "polyphenolics"), which are a group of chemical substances found in plants, characterized by the presence of more than one phenol group per molecule. A variety of health benefits may derived from polyphenols, including prevention of cancer, heart disease, and chronic inflammatory disease and improved mental strength and physical strength, for example. Suitable polyphenols for embodiments of this invention, include catechins, proanthocyanidins, procyanidins, anthocyanins, quercerin, rutin, reservatrol, isoflavones, curcumin, punicalagin, ellagitannin, hesperidin, naringin, citrus flavonoids, chlorogenic acid, other similar materials, and combinations thereof.

In particular embodiments, the antioxidant is a catechin such as, for example, epigallocatechin gallate (EGCG). Suitable sources of catechins for embodiments of this invention include, but are not limited to, green tea, white tea, black tea, oolong tea, chocolate, cocoa, red wine, grape seed, red grape skin, purple grape skin, red grape juice, purple grape juice, berries, pycnogenol, and red apple peel.

In some embodiments, the antioxidant is chosen from proanthocyanidins, procyanidins or combinations thereof. Suitable sources of proanthocyanidins and procyanidins for embodiments of this invention include, but are not limited to, red grapes, purple grapes, cocoa, chocolate, grape seeds, red wine, cacao beans, cranberry, apple peel, plum, blueberry, black currants, choke berry, green tea, sorghum, cinnamon, barley, red kidney bean, pinto bean, hops, almonds, hazelnuts, pecans, pistachio, pycnogenol, and colorful berries.

In particular embodiments, the antioxidant is a anthocyanin. Suitable sources of anthocyanins for embodiments of this invention include, but are not limited to, red berries, blueberries, bilberry, cranberry, raspberry, cherry, pomegranate, strawberry, elderberry, choke berry, red grape skin, purple grape skin, grape seed, red wine, black currant, red currant, cocoa, plum, apple peel, peach, red pear, red cabbage, red onion, red orange, and blackberries.

In some embodiments, the antioxidant is chosen from quercetin, rutin or combinations thereof. Suitable sources of quercetin and rutin for embodiments of this invention include, but are not limited to, red apples, onions, kale, bog whortleberry, lingonberrys, chokeberry, cranberry, blackberry, blueberry, strawberry, raspberry, black currant, green tea, black tea, plum, apricot, parsley, leek, broccoli, chili pepper, berry wine, and ginkgo.

In some embodiments, the antioxidant is resveratrol. Suitable sources of resveratrol for embodiments of this invention include, but are not limited to, red grapes, peanuts, cranberry, blueberry, bilberry, mulberry, Japanese Itadori tea, and red wine.

In particular embodiments, the antioxidant is an isoflavone. Suitable sources of isoflavones for embodiments of this invention include, but are not limited to, soy beans, soy products, legumes, alfalfa sprouts, chickpeas, peanuts, and red clover.

In some embodiments, the antioxidant is curcumin. Suitable sources of curcumin for embodiments of this invention include, but are not limited to, turmeric and mustard.

In particular embodiments, the antioxidant is chosen from punicalagin, ellagitannin or combinations thereof. Suitable sources of punicalagin and ellagitannin for embodiments of this invention include, but are not limited to, pomegranate, raspberry, strawberry, walnut, and oak-aged red wine.

In some embodiments, the antioxidant is a citrus flavonoid, such as hesperidin or naringin. Suitable sources of citrus flavonids, such as hesperidin or naringin, for embodiments of this invention include, but are not limited to, oranges, grapefruits, and citrus juices.

In particular embodiments, the antioxidant is chlorogenic acid. Suitable sources of chlorogenic acid for embodiments of this invention include, but are not limited to, green coffee, yerba mate, red wine, grape seed, red grape skin, purple grape skin, red grape juice, purple grape juice, apple juice, cranberry, pomegranate, blueberry, strawberry, sunflower, *Echinacea*, pycnogenol, and apple peel.

Dietary Fiber

In certain embodiments, the functional ingredient is at least one dietary fiber source. Generally, according to particular embodiments of this invention, the at least one dietary fiber source is present in the edible product, e.g. beverage, in an amount sufficient to promote health and wellness.

Numerous polymeric carbohydrates having significantly different structures in both composition and linkages fall within the definition of dietary fiber. Such compounds are well known to those skilled in the art, non-limiting examples of which include non-starch polysaccharides, lignin, cellulose, methylcellulose, the hemicelluloses, β-glucans, pectins, gums, mucilage, waxes, inulins, oligosaccharides, fructooligosaccharides, cyclodextrins, chitins, and combinations thereof.

Polysaccharides are complex carbohydrates composed of monosaccharides joined by glycosidic linkages. Non-starch polysaccharides are bonded with β-linkages, which humans are unable to digest due to a lack of an enzyme to break the β-linkages. Conversely, digestible starch polysaccharides generally comprise α(1-4) linkages.

Lignin is a large, highly branched and cross-linked polymer based on oxygenated phenylpropane units. Cellulose is a linear polymer of glucose molecules joined by a β(1-4) linkage, which mammalian amylases are unable to hydrolyze. Methylcellulose is a methyl esther of cellulose that is often used in foodstuffs as a thickener, and emulsifier. It is commercially available (e.g., Citrucel by GlaxoSmithKline, Celevac by Shire Pharmaceuticals). Hemicelluloses are highly branched polymers consisting mainly of glucurono- and 4-O-methylglucuroxylans. β-Glucans are mixed-linkage (1-3), (1-4) β-D-glucose polymers found primarily in cereals, such as oats and barley. Pectins, such as beta pectin, are a group of polysaccharides composed primarily of D-galacturonic acid, which is methoxylated to variable degrees.

Gums and mucilages represent a broad array of different branched structures. Guar gum, derived from the ground endosperm of the guar seed, is a galactomannan. Guar gum is commercially available (e.g., Benefiber by Novartis AG). Other gums, such as gum arabic andpectins, have still different structures. Still other gums include xanthan gum, gellan gum, tara gum, psylium seed husk gum, and locust been gum.

Waxes are esters of ethylene glycol and two fatty acids, generally occurring as a hydrophobic liquid that is insoluble in water.

Inulins comprise naturally occurring oligosaccharides belonging to a class of carbohydrates known as fructans. They generally are comprised of fructose units joined by β(2-1) glycosidic linkages with a terminal glucose unit. Oligosaccharides are saccharide polymers containing typically three to six component sugars. They are generally found either O- or N-linked to compatible amino acid side chains in proteins or to lipid molecules. Fructooligosaccharides are oligosaccharides consisting of short chains of fructose molecules.

Cyclodextrins are a family of cyclic oligosaccharides composed of α-D-glucopyranoside units. They can be produced from starch by means of enzymatic conversion. α-Cyclodextrin is a six sugar ring molecule, whereas β- and γ-cyclodextrins have seven and eight sugar ring molecules, respectively. Non-cyclic dextrins are known as maltodextrins and are generally easily digested by humans. Digestion resistant maltodextrin is commercially available (e.g., Fibersol-2 by ADM).

Food sources of dietary fiber include, but are not limited to, grains, legumes, fruits, and vegetables. Grains providing dietary fiber include, but are not limited to, oats, rye, barley, wheat. Legumes providing fiber include, but are not limited to, peas and beans such as soybeans. Fruits and vegetables providing a source of fiber include, but are not limited to, apples, oranges, pears, bananas, berries, tomatoes, green beans, broccoli, cauliflower, carrots, potatoes, celery. Plant foods such as bran, nuts, and seeds (such as flax seeds) are also sources of dietary fiber. Parts of plants providing dietary fiber include, but are not limited to, the stems, roots, leaves, seeds, pulp, and skin.

Although dietary fiber generally is derived from plant sources, indigestible animal products such as chitins are also classified as dietary fiber. Chitin is a polysaccharide composed of units of acetylglucosamine joined by β(1-4) linkages, similar to the linkages of cellulose.

Sources of dietary fiber often are divided into categories of soluble and insoluble fiber based on their solubility in water. Both soluble and insoluble fibers are found in plant foods to varying degrees depending upon the characteristics of the plant. Although insoluble in water, insoluble fiber has passive hydrophilic properties that help increase bulk, soften stools, and shorten transit time of fecal solids through the intestinal tract.

Unlike insoluble fiber, soluble fiber readily dissolves in water. Soluble fiber undergoes active metabolic processing via fermentation in the colon, increasing the colonic microflora and thereby increasing the mass of fecal solids. Fermentation of fibers by colonic bacteria also yields end-products with significant health benefits. For example, fermentation of the food masses produces gases and short-chain fatty acids. Acids produced during fermentation include butyric, acetic, propionic, and valeric acids that have various beneficial properties such as stabilizing blood glucose levels by acting on pancreatic insulin release and providing liver control by glycogen breakdown. In addition, fiber fermentation may reduce atherosclerosis by lowering cholesterol synthesis by the liver and reducing blood levels of LDL and triglycerides. The acids produced during fermentation lower colonic pH, thereby protecting the colon lining from cancer polyp formation. The lower colonic pH also increases mineral absorption, improves the barrier properties of the colonic mucosal layer, and inhibits inflammatory and adhesion irritants. Fermentation of fibers also may benefit the immune system by stimulating production of T-helper cells, antibodies, leukocytes, splenocytes, cytokinins and lymphocytes.

Fatty Acid

In certain embodiments, the functional ingredient is at least one fatty acid. Generally, according to particular embodiments of this invention, the at least one fatty acid is present in the edible product, e.g. beverage, in an amount sufficient to promote health and wellness.

As used herein, "fatty acid" refers to any straight chain monocarboxylic acid and includes saturated fatty acids, unsaturated fatty acids, long chain fatty acids, medium chain fatty acids, short chain fatty acids, fatty acid precursors (including omega-9 fatty acid precursors), and esterified fatty acids. As used herein, "long chain polyunsaturated fatty acid" refers to any polyunsaturated carboxylic acid or organic acid with a long aliphatic tail. As used herein, "omega-3 fatty acid" refers to any polyunsaturated fatty acid having a first double bond as the third carbon-carbon bond from the terminal methyl end of its carbon chain. In particular embodiments, the omega-3 fatty acid may comprise a long chain omega-3 fatty acid. As used herein, "omega-6 fatty acid" any polyunsaturated fatty acid having a first double bond as the sixth carbon-carbon bond from the terminal methyl end of its carbon chain.

Suitable omega-3 fatty acids for use in embodiments of the present invention can be derived from algae, fish, animals, plants, or combinations thereof, for example. Examples of suitable omega-3 fatty acids include, but are not limited to, linolenic acid, alpha-linolenic acid, eicosapentaenoic acid, docosahexaenoic acid, stearidonic acid, eicosatetraenoic acid and combinations thereof. In some embodiments, suitable omega-3 fatty acids can be provided in fish oils, (e.g., menhaden oil, tuna oil, salmon oil, bonito oil, and cod oil), microalgae omega-3 oils or combinations thereof. In particular embodiments, suitable omega-3 fatty acids may be derived from commercially available omega-3 fatty acid oils such as Microalgae DHA oil (from Martek, Columbia, Md.), OmegaPure (from Omega Protein, Houston, Tex.), Marinol C-38 (from Lipid Nutrition, Channahon, Ill.), Bonito oil and MEG-3 (from Ocean Nutrition, Dartmouth, NS), Evogel (from Symrise, Holzminden, Germany), Marine Oil, from tuna or salmon (from Arista Wilton, Conn.), OmegaSource 2000, Marine Oil, from menhaden and Marine Oil, from cod (from OmegaSource, RTP, NC).

Suitable omega-6 fatty acids include, but are not limited to, linoleic acid, gamma-linolenic acid, dihommo-gamma-linolenic acid, arachidonic acid, eicosadienoic acid, docosa-dienoic acid, adrenic acid, docosapentaenoic acid and combinations thereof.

Suitable esterified fatty acids for embodiments of the present invention may include, but are not limited to, monoacylglycerols containing omega-3 and/or omega-6 fatty acids, diacylglycerols containing omega-3 and/or omega-6 fatty acids, or triacylglycerols containing omega-3 and/or omega-6 fatty acids and combinations thereof.

Vitamin

In certain embodiments, the functional ingredient is at least one vitamin. Generally, according to particular embodiments of this invention, the at least one vitamin is present in the edible product, e.g. beverage, in an amount sufficient to promote health and wellness.

Vitamins are organic compounds that the human body needs in small quantities for normal functioning. The body uses vitamins without breaking them down, unlike other nutrients such as carbohydrates and proteins. To date, thirteen vitamins have been recognized, and one or more can be used in the sweetened compositions herein. Suitable vitamins include, vitamin A, vitamin D, vitamin E, vitamin K, vitamin B1, vitamin B2, vitamin B3, vitamin B5, vitamin B6, vitamin B7, vitamin B9, vitamin B12, and vitamin C. Many of vitamins also have alternative chemical names, non-limiting examples of which are provided below.

| Vitamin | Alternative names |
| --- | --- |
| Vitamin A | Retinol |
|  | Retinaldehyde |
|  | Retinoic acid |
|  | Retinoids |
|  | Retinal |
|  | Retinoic ester |
| Vitamin D | Calciferol |
| (vitamins D1-D5) | Cholecalciferol |
|  | Lumi sterol |
|  | Ergocalciferol |
|  | Dihydrotachysterol |
|  | 7-dehydrocholesterol |
| Vitamin E | Tocopherol |
|  | Tocotrienol |
| Vitamin K | Phylloquinone |
|  | Naphthoquinone |
| Vitamin B1 | Thiamin |
| Vitamin B2 | Riboflavin |
|  | Vitamin G |
| Vitamin | Alternative names |
| Vitamin B3 | Niacin |
|  | Nicotinic acid |
|  | Vitamin PP |
| Vitamin B5 | Pantothenic acid |

-continued

| Vitamin | Alternative names |
| --- | --- |
| Vitamin B6 | Pyridoxine |
|  | Pyridoxal |
|  | Pyridoxamine |
| Vitamin B7 | Biotin |
|  | Vitamin H |
| Vitamin B9 | Folic acid |
|  | Folate |
|  | Folacin |
|  | Vitamin M |
|  | Pteroyl-L-glutamic acid |
| Vitamin B12 | Cobalamin |
|  | Cyanocobalamin |
| Vitamin C | Ascorbic Acid |

Various other compounds have been classified as vitamins by some authorities. These compounds may be termed pseudo-vitamins and include, but are not limited to, compounds such as ubiquinone (coenzyme Q10), pangamic acid, dimethylglycine, taestrile, amygdaline, flavanoids, para-aminobenzoic acid, adenine, adenylic acid, and s-methyl-methionine. As used herein, the term vitamin includes pseudo-vitamins.

In some embodiments, the vitamin is a fat-soluble vitamin chosen from vitamin A, D, E, K and combinations thereof.

In other embodiments, the vitamin is a water-soluble vitamin chosen from vitamin B1, vitamin B2, vitamin B3, vitamin B6, vitamin B12, folic acid, biotin, pantothenic acid, vitamin C and combinations thereof.

Glucosamine

In certain embodiments, the functional ingredient is glucosamine. Generally, according to particular embodiments of this invention, glucosamine is present in the edible product, e.g. beverage, in an amount sufficient to promote health and wellness.

Glucosamine, also called chitosamine, is an amino sugar that is believed to be an important precursor in the biochemical synthesis of glycosylated proteins and lipids. D-glucosamine occurs naturally in the cartilage in the form of glucosamine-6-phosphate, which is synthesized from fructose-6-phosphate and glutamine. However, glucosamine also is available in other forms, non-limiting examples of which include glucosamine hydrochloride, glucosamine sulfate, N-acetyl-glucosamine, or any other salt forms or combinations thereof. Glucosamine may be obtained by acid hydrolysis of the shells of lobsters, crabs, shrimps, or prawns using methods well known to those of ordinary skill in the art. In a particular embodiment, glucosamine may be derived from fungal biomass containing chitin, as described in U.S. Patent Publication No. 2006/0172392.

The sweetened composition can further comprise chondroitin sulfate.

Mineral

In certain embodiments, the functional ingredient is at least one mineral. Generally, according to particular embodiments of this invention, the at least one mineral is present in the edible product, e.g. beverage, in an amount sufficient to promote health and wellness.

Minerals, in accordance with the teachings of this invention, comprise inorganic chemical elements required by living organisms. Minerals are comprised of a broad range of compositions (e.g., elements, simple salts, and complex silicates) and also vary broadly in crystalline structure. They may naturally occur in foods and beverages, may be added as a supplement, or may be consumed or administered separately from foods or beverages.

Minerals may be categorized as either bulk minerals, which are required in relatively large amounts, or trace minerals, which are required in relatively small amounts. Bulk minerals generally are required in amounts greater than or equal to about 100 mg per day and trace minerals are those that are required in amounts less than about 100 mg per day.

In particular embodiments of this invention, the mineral is chosen from bulk minerals, trace minerals or combinations thereof. Non-limiting examples of bulk minerals include calcium, chlorine, magnesium, phosphorous, potassium, sodium, and sulfur. Non-limiting examples of trace minerals include chromium, cobalt, copper, fluorine, iron, manganese, molybdenum, selenium, zinc, and iodine. Although iodine generally is classified as a trace mineral, it is required in larger quantities than other trace minerals and often is categorized as a bulk mineral.

In other particular embodiments of this invention, the mineral is a trace mineral, believed to be necessary for human nutrition, non-limiting examples of which include bismuth, boron, lithium, nickel, rubidium, silicon, strontium, tellurium, tin, titanium, tungsten, and vanadium.

The minerals embodied herein may be in any form known to those of ordinary skill in the art. For example, in a particular embodiment the minerals may be in their ionic form, having either a positive or negative charge. In another particular embodiment the minerals may be in their molecular form. For example, sulfur and phosphorous often are found naturally as sulfates, sulfides, and phosphates.

Preservative

In certain embodiments, the functional ingredient is at least one preservative. Generally, according to particular embodiments of this invention, the at least one preservative is present in the edible product, e.g. beverage, in an amount sufficient to promote health and wellness.

In particular embodiments of this invention, the preservative is chosen from antimicrobials, antioxidants, antienzymatics or combinations thereof. Non-limiting examples of antimicrobials include sulfites, propionates, benzoates, sorbates, nitrates, nitrites, bacteriocins, salts, sugars, acetic acid, dimethyl dicarbonate (DMDC), ethanol, and ozone.

According to a particular embodiment, the preservative is a sulfite. Sulfites include, but are not limited to, sulfur dioxide, sodium bisulfite, and potassium hydrogen sulfite.

According to another particular embodiment, the preservative is a propionate. Propionates include, but are not limited to, propionic acid, calcium propionate, and sodium propionate.

According to yet another particular embodiment, the preservative is a benzoate. Benzoates include, but are not limited to, sodium benzoate and benzoic acid.

In another particular embodiment, the preservative is a sorbate. Sorbates include, but are not limited to, potassium sorbate, sodium sorbate, calcium sorbate, and sorbic acid.

In still another particular embodiment, the preservative is a nitrate and/or a nitrite. Nitrates and nitrites include, but are not limited to, sodium nitrate and sodium nitrite.

In yet another particular embodiment, the at least one preservative is a bacteriocin, such as, for example, nisin.

In another particular embodiment, the preservative is ethanol.

In still another particular embodiment, the preservative is ozone.

Non-limiting examples of antienzymatics suitable for use as preservatives in particular embodiments of the invention include ascorbic acid, citric acid, and metal chelating agents such as ethylenediaminetetraacetic acid (EDTA).

Hydration Agent

In certain embodiments, the functional ingredient is at least one hydration agent. Generally, according to particular embodiments of this invention, the at least one hydration agent is present in the edible product, e.g. beverage, in an amount sufficient to promote health and wellness.

Hydration products help the body to replace fluids that are lost through excretion. For example, fluid is lost as sweat in order to regulate body temperature, as urine in order to excrete waste substances, and as water vapor in order to exchange gases in the lungs. Fluid loss can also occur due to a wide range of external causes, non-limiting examples of which include physical activity, exposure to dry air, diarrhea, vomiting, hyperthermia, shock, blood loss, and hypotension. Diseases causing fluid loss include diabetes, cholera, gastroenteritis, shigellosis, and yellow fever. Forms of malnutrition that cause fluid loss include the excessive consumption of alcohol, electrolyte imbalance, fasting, and rapid weight loss.

In a particular embodiment, the hydration product is a composition that helps the body replace fluids that are lost during exercise. Accordingly, in a particular embodiment, the hydration product is an electrolyte, non-limiting examples of which include sodium, potassium, calcium, magnesium, chloride, phosphate, bicarbonate, and combinations thereof. Suitable electrolytes for use in particular embodiments of this invention are also described in U.S. Pat. No. 5,681,569, the disclosure of which is expressly incorporated herein by reference. In particular embodiments, the electrolytes are obtained from their corresponding water-soluble salts. Non-limiting examples of salts for use in particular embodiments include chlorides, carbonates, sulfates, acetates, bicarbonates, citrates, phosphates, hydrogen phosphates, tartates, sorbates, citrates, benzoates, or combinations thereof. In other embodiments, the electrolytes are provided by juice, fruit extracts, vegetable extracts, tea, or teas extracts.

In particular embodiments of this invention, the hydration product is a carbohydrate to supplement energy stores burned by muscles. Suitable carbohydrates for use in particular embodiments of this invention are described in U.S. Pat. Nos. 4,312,856, 4,853,237, 5,681,569, and 6,989,171, the disclosures of which are expressly incorporated herein by reference. Non-limiting examples of suitable carbohydrates include monosaccharides, disaccharides, oligosaccharides, complex polysaccharides or combinations thereof. Non-limiting examples of suitable types of monosaccharides for use in particular embodiments include trioses, tetroses, pentoses, hexoses, heptoses, octoses, and nonoses. Non-limiting examples of specific types of suitable monosaccharides include glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, and sialose. Non-limiting examples of suitable disaccharides include sucrose, lactose, and maltose. Non-limiting examples of suitable oligosaccharides include saccharose, maltotriose, and maltodextrin. In other particular embodiments, the carbohydrates are provided by a corn syrup, a beet sugar, a cane sugar, a juice, or a tea.

In another particular embodiment, the hydration is a flavanol that provides cellular rehydration. Flavanols are a class of natural substances present in plants, and generally comprise a 2-phenylbenzopyrone molecular skeleton attached to one or more chemical moieties. Non-limiting examples of suitable flavanols for use in particular embodiments of this invention include catechin, epicatechin, gallocatechin, epigallocatechin, epicatechin gallate, epigallocatechin 3-gallate, theaflavin, theaflavin 3-gallate, theaflavin 3'-gallate, theaflavin 3,3' gallate, thearubigin or combinations thereof. Several common sources of flavanols include tea plants, fruits, vegetables, and flowers. In preferred embodiments, the flavanol is extracted from green tea.

In a particular embodiment, the hydration product is a glycerol solution to enhance exercise endurance. The ingestion of a glycerol containing solution has been shown to provide beneficial physiological effects, such as expanded blood volume, lower heart rate, and lower rectal temperature.

Probiotics/Probiotics

In certain embodiments, the functional ingredient is chosen from at least one probiotic, prebiotic and combination thereof. Generally, according to particular embodiments of this invention, the at least one probiotic, prebiotic or combination thereof is present in the edible product, e.g. beverage, in an amount sufficient to promote health and wellness.

Probiotics, in accordance with the teachings of this invention, comprise microorganisms that benefit health when consumed in an effective amount. Desirably, probiotics beneficially affect the human body's naturally-occurring gastrointestinal microflora and impart health benefits apart from nutrition. Probiotics may include, without limitation, bacteria, yeasts, and fungi.

According to particular embodiments, the probiotic is a beneficial microorganisms that beneficially affects the human body's naturally-occurring gastrointestinal microflora and imparts health benefits apart from nutrition. Examples of probiotics include, but are not limited to, bacteria of the genus *Lactobacilli*, *Bifidobacteria*, *Streptococci*, or combinations thereof, that confer beneficial effects to humans.

In particular embodiments of the invention, the at least one probiotic is chosen from the genus *Lactobacilli*. *Lactobacilli* (i.e., bacteria of the genus *Lactobacillus*, hereinafter "L.") have been used for several hundred years as a food preservative and for promoting human health. Non-limiting examples of species of *Lactobacilli* found in the human intestinal tract include *L. acidophilus*, *L. casei*, *L. fermentum*, *L. salvia roes*, *L. brevis*, *L. leichmannii*, *L. plantarum*, *L. cellobiosus*, *L. reuteri*, *L. rhamnosus*, *L. GG*, *L. bulgaricus*, and *L. thermophilus*.

According to other particular embodiments of this invention, the probiotic is chosen from the genus *Bifidobacteria*. *Bifidobacteria* also are known to exert a beneficial influence on human health by producing short chain fatty acids (e.g., acetic, propionic, and butyric acids), lactic, and formic acids as a result of carbohydrate metabolism. Non-limiting species of *Bifidobacteria* found in the human gastrointestinal tract include *B. angulatum*, *B. animalis*, *B. asteroides*, *B. bifidum*, *B. boum*, *B. breve*, *B. catenulatum*, *B. choerinum*, *B. coryneforme*, *B. cuniculi*, *B. dentium*, *B. gallicum*, *B. gallinarum*, *B indicum*, *B. longum*, *B. magnum*, *B. merycicum*, *B. minimum*, *B. pseudocatenulatum*, *B. pseudolongum*, *B. psychraerophilum*, *B. pullorum*, *B. ruminantium*, *B. saeculare*, *B. scardovii*, *B. simiae*, *B. subtile*, *B. thermacidophilum*, *B. thermophilum*, *B. urinalis*, and B. sp.

According to other particular embodiments of this invention, the probiotic is chosen from the genus *Streptococcus*. *Streptococcus thermophilus* is a gram-positive facultative anaerobe. It is classified as a lactic acid bacteria and commonly is found in milk and milk products, and is used in the production of yogurt. Other non-limiting probiotic species of this bacteria include *Streptococcus salivarus* and *Streptococcus cremoris*.

Probiotics that may be used in accordance with this invention are well-known to those of skill in the art. Non-limiting examples of foodstuffs comprising probiotics include yogurt, sauerkraut, kefir, kimchi, fermented vegetables, and other foodstuffs containing a microbial element that beneficially affects the host animal by improving the intestinal microbalance.

Prebiotics, in accordance with the teachings of this invention, are compositions that promote the growth of beneficial bacteria in the intestines. Prebiotic substances can be consumed by a relevant probiotic, or otherwise assist in keeping the relevant probiotic alive or stimulate its growth. When consumed in an effective amount, prebiotics also beneficially affect the human body's naturally-occurring gastrointestinal microflora and thereby impart health benefits apart from just nutrition. Prebiotic foods enter the colon and serve as substrate for the endogenous bacteria, thereby indirectly providing the host with energy, metabolic substrates, and essential micronutrients. The body's digestion and absorption of prebiotic foods is dependent upon bacterial metabolic activity, which salvages energy for the host from nutrients that escaped digestion and absorption in the small intestine.

Prebiotics, in accordance with the embodiments of this invention, include, without limitation, mucopolysaccharides, oligosaccharides, polysaccharides, amino acids, vitamins, nutrient precursors, proteins and combinations thereof.

According to a particular embodiment of this invention, the prebiotic is chosen from dietary fibers, including, without limitation, polysaccharides and oligosaccharides. These compounds have the ability to increase the number of probiotics, which leads to the benefits conferred by the probiotics. Non-limiting examples of oligosaccharides that are categorized as prebiotics in accordance with particular embodiments of this invention include fructooligosaccharides, inulins, isomalto-oligosaccharides, lactilol, lactosucrose, lacto-oligosaccharides, fucose-containing-oligosaccharides, lactulose, pyrodextrins, soy oligosaccharides, transgalacto-oligosaccharides, and xylo-oligosaccharides.

According to other particular embodiments of the invention, the prebiotic is an amino acid. Although a number of known prebiotics break down to provide carbohydrates for probiotics, some probiotics also require amino acids for nourishment.

Prebiotics are found naturally in a variety of foods including, without limitation, bananas, berries, asparagus, garlic, wheat, oats, barley (and other whole grains), flaxseed, tomatoes, Jerusalem artichoke, onions and chicory, greens (e.g., dandelion greens, spinach, collard greens, chard, kale, mustard greens, turnip greens), and legumes (e.g., lentils, kidney beans, chickpeas, navy beans, white beans, black beans).

Weight Management Agent

In certain embodiments, the functional ingredient is at least one weight management agent. Generally, according to particular embodiments of this invention, the at least one weight management agent is present in the edible product, e.g. beverage, in an amount sufficient to promote health and wellness.

As used herein, "a weight management agent" includes an appetite suppressant and/or a thermogenesis agent. As used herein, the phrases "appetite suppressant", "appetite satiation compositions", "satiety agents", and "satiety ingredients" are synonymous. The phrase "appetite suppressant"

describes macronutrients, herbal extracts, exogenous hormones, anorectics, anorexigenics, pharmaceutical drugs, and combinations thereof, that when delivered in an effective amount, suppress, inhibit, reduce, or otherwise curtail a person's appetite. The phrase "thermogenesis agent" describes macronutrients, herbal extracts, exogenous hormones, anorectics, anorexigenics, pharmaceutical drugs, and combinations thereof, that when delivered in an effective amount, activate or otherwise enhance a person's thermogenesis or metabolism.

Suitable weight management agents include macronutrient selected from the group consisting of proteins, carbohydrates, dietary fats, and combinations thereof. Consumption of proteins, carbohydrates, and dietary fats stimulates the release of peptides with appetite-suppressing effects. For example, consumption of proteins and dietary fats stimulates the release of the gut hormone cholecytokinin (CCK), while consumption of carbohydrates and dietary fats stimulates release of Glucagon-like peptide 1 (GLP-1).

Suitable macronutrient weight management agents also include carbohydrates. Carbohydrates generally comprise sugars, starches, cellulose and gums that the body converts into glucose for energy. Carbohydrates often are classified into two categories, digestible carbohydrates (e.g., monosaccharides, disaccharides, and starch) and non-digestible carbohydrates (e.g., dietary fiber). Studies have shown that non-digestible carbohydrates and complex polymeric carbohydrates having reduced absorption and digestibility in the small intestine stimulate physiologic responses that inhibit food intake. Accordingly, the carbohydrates embodied herein desirably comprise non-digestible carbohydrates or carbohydrates with reduced digestibility. Non-limiting examples of such carbohydrates include polydextrose; inulin; monosaccharide-derived polyols such as erythritol, mannitol, xylitol, and sorbitol; disaccharide-derived alcohols such as isomalt, lactitol, and maltitol; and hydrogenated starch hydrolysates. Carbohydrates are described in more detail herein below.

In another particular embodiment weight management agents is dietary fat. Dietary fats are lipids comprising combinations of saturated and unsaturated fatty acids. Polyunsaturated fatty acids have been shown to have a greater satiating power than mono-unsaturated fatty acids. Accordingly, the dietary fats embodied herein desirably comprise poly-unsaturated fatty acids, non-limiting examples of which include triacylglycerols.

In a particular embodiment, the weight management agents is an herbal extract. Extracts from numerous types of plants have been identified as possessing appetite suppressant properties. Non-limiting examples of plants whose extracts have appetite suppressant properties include plants of the genus *Hoodia, Trichocaulon, Caralluma, Stapelia, Orbea, Asclepias*, and *Camelia*. Other embodiments include extracts derived from *Gymnema Sylvestre*, Kola Nut, Citrus Auran tium, Yerba Mate, *Griffonia Simplicifolia*, Guarana, myrrh, guggul Lipid, and black current seed oil.

The herbal extracts may be prepared from any type of plant material or plant biomass. Non-limiting examples of plant material and biomass include the stems, roots, leaves, dried powder obtained from the plant material, and sap or dried sap. The herbal extracts generally are prepared by extracting sap from the plant and then spray-drying the sap. Alternatively, solvent extraction procedures may be employed. Following the initial extraction, it may be desirable to further fractionate the initial extract (e.g., by column chromatography) in order to obtain an herbal extract with enhanced activity. Such techniques are well known to those of ordinary skill in the art.

In a particular embodiment, the herbal extract is derived from a plant of the genus *Hoodia*, species of which include *H. alstonii, H. currorii, H. dregei, H. flava, H. gordonii, H. jutatae, H. mossamedensis, H. officinalis, H. parviflorai, H. pedicellata, H. pilifera, H. ruschii*, and *H. triebneri*. *Hoodia* plants are stem succulents native to southern Africa. A sterol glycoside of *Hoodia*, known as P57, is believed to be responsible for the appetite-suppressant effect of the *Hoodia* species.

In another particular embodiment, the herbal extract is derived from a plant of the genus *Caralluma*, species of which include *C. indica, C. fimbriata, C. attenuate, C. tuberculata, C. edulis, C. adscendens, C. stalagmifera, C. umbellate, C. penicillata, C. russeliana, C. retrospicens, C. Arabica*, and *C. lasiantha*. *Carralluma* plants belong to the same Subfamily as *Hoodia*, Asclepiadaceae. *Caralluma* are small, erect and fleshy plants native to India having medicinal properties, such as appetite suppression, that generally are attributed to glycosides belonging to the pregnane group of glycosides, non-limiting examples of which include caratuberside A, caratuberside B, bouceroside I, bouceroside II, bouceroside III, bouceroside IV, bouceroside V, bouceroside VI, bouceroside VII, bouceroside VIII, bouceroside IX, and bouceroside X.

In another particular embodiment, the at least one herbal extract is derived from a plant of the genus *Trichocaulon*. *Trichocaulon* plants are succulents that generally are native to southern Africa, similar to *Hoodia*, and include the species *T. piliferum* and *T officinale*.

In another particular embodiment, the herbal extract is derived from a plant of the genus *Stapelia* or *Orbea*, species of which include *S. gigantean* and *O. variegate*, respectively. Both *Stapelia* and *Orbea* plants belong to the same Subfamily as *Hoodia*, Asclepiadaceae. Not wishing to be bound by any theory, it is believed that they compounds exhibiting appetite suppressant activity are saponins, such as pregnane glycosides, which include stavarosides A, B, C, D, E, F, G, H, I, J, and K.

In another particular embodiment, the herbal extract is derived from a plant of the genus *Asclepias*. *Asclepias* plants also belong to the Asclepiadaceae family of plants. Non-limiting examples of *Asclepias* plants include *A. incarnate, A. curassayica, A. syriaca*, and *A. tuberose*. Not wishing to be bound by any theory, it is believed that the extracts comprise steroidal compounds, such as pregnane glycosides and pregnane aglycones, having appetite suppressant effects.

In a particular embodiment, the weight management agent is an exogenous hormone having a weight management effect. Non-limiting examples of such hormones include CCK, peptide YY, ghrelin, bombesin and gastrin-releasing peptide (GRP), enterostatin, apolipoprotein A-IV, GLP-1, amylin, somastatin, and leptin.

In another embodiment, the weight management agent is a pharmaceutical drug. Non-limiting examples include phentenime, diethylpropion, phendimetrazine, sibutramine, rimonabant, oxyntomodulin, floxetine hydrochloride, ephedrine, phenethylamine, or other stimulants.

The at least one weight management agent may be utilized individually or in combination as a functional ingredient for the sweetened compositions provided in this invention.

Osteoporosis Management Agent

In certain embodiments, the functional ingredient is at least one osteoporosis management agent. Generally, according to particular embodiments of this invention, the at least one osteoporosis management agent is present in the edible product, e.g. beverage, in an amount sufficient to promote health and wellness.

Osteoporosis is a skeletal disorder of compromised bone strength, resulting in an increased risk of bone fracture. Generally, osteoporosis is characterized by reduction of the bone mineral density (BMD), disruption of bone microarchitecture, and changes to the amount and variety of non-collagenous proteins in the bone.

In certain embodiments, the osteoporosis management agent is at least one calcium source. According to a particular embodiment, the calcium source is any compound containing calcium, including salt complexes, solubilized species, and other forms of calcium. Non-limiting examples of calcium sources include amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium citrate malate, calcium gluconate, calcium tartrate, calcium lactate, solubilized species thereof, and combinations thereof.

According to a particular embodiment, the osteoporosis management agent is a magnesium source. The magnesium source is any compound containing magnesium, including salt complexes, solubilized species, and other forms of magnesium. Non-limiting examples of magnesium sources include magnesium chloride, magnesium citrate, magnesium gluceptate, magnesium gluconate, magnesium hydroxide, magnesium picolate, magnesium sulfate, solubilized species thereof, and mixtures thereof. In another particular embodiment, the magnesium source comprises an amino acid chelated or creatine chelated magnesium.

In other embodiments, the osteoporosis agent is chosen from vitamins D, C, K, their precursors and/or beta-carotene and combinations thereof.

Numerous plants and plant extracts also have been identified as being effective in the prevention and treatment of osteoporosis. Not wishing to be bound by any theory, it is believed that the plants and plant extracts stimulates bone morphogenic proteins and/or inhibits bone resorption, thereby stimulating bone regeneration and strength. Non-limiting examples of suitable plants and plant extracts as osteoporosis management agents include species of the genus *Taraxacum* and *Amelanchier*, as disclosed in U.S. Patent Publication No. 2005/0106215, and species of the genus *Lindera, Artemisia, Acorus, Carthamus, Carum, Cnidium, Curcuma, Cyperus, Juniperus, Prunus, Iris, Cichorium, Dodonaea, Epimedium, Erigonoum, Soya, Mentha, Ocimum, thymus, Tanacetum, Plantago, Spearmint, Bixa, Vitis, Rosemarinus, Rhus,* and *Anethum,* as disclosed in U.S. Patent Publication No. 2005/0079232.

Phytoestrogen

In certain embodiments, the functional ingredient is at least one phytoestrogen. Generally, according to particular embodiments of this invention, the at least one phytoestrogen is present in the edible product, e.g. beverage, in an amount sufficient to promote health and wellness.

Phytoestrogens are compounds found in plants which can typically be delivered into human bodies by ingestion of the plants or the plant parts having the phytoestrogens. As used herein, "phytoestrogen" refers to any substance which, when introduced into a body causes an estrogen-like effect of any degree. For example, a phytoestrogen may bind to estrogen receptors within the body and have a small estrogen-like effect.

Examples of suitable phytoestrogens for embodiments of this invention include, but are not limited to, isoflavones, stilbenes, lignans, resorcyclic acid lactones, coumestans, coumestrol, equol, and combinations thereof. Sources of suitable phytoestrogens include, but are not limited to, whole grains, cereals, fibers, fruits, vegetables, black cohosh, agave root, black currant, black haw, chasteberries, cramp bark, dong quai root, devil's club root, false unicorn root, *ginseng* root, groundsel herb, licorice, liferoot herb, motherwort herb, peony root, raspberry leaves, rose family plants, sage leaves, sarsaparilla root, saw palmetto berried, wild yam root, yarrow blossoms, legumes, soybeans, soy products (e.g., miso, soy flour, soymilk, soy nuts, soy protein isolate, tempen, or tofu) chick peas, nuts, lentils, seeds, clover, red clover, dandelion leaves, dandelion roots, fenugreek seeds, green tea, hops, red wine, flaxseed, garlic, onions, linseed, borage, butterfly weed, caraway, chaste tree, vitex, dates, dill, fennel seed, gotu kola, milk thistle, pennyroyal, pomegranates, southernwood, soya flour, tansy, and root of the kudzu vine (*pueraria* root) and the like, and combinations thereof.

Isoflavones belong to the group of phytonutrients called polyphenols. In general, polyphenols (also known as "polyphenolics"), are a group of chemical substances found in plants, characterized by the presence of more than one phenol group per molecule.

Suitable phytoestrogcn isoflavones in accordance with embodiments of this invention include genistein, daidzein, glycitein, biochanin A, formononetin, their respective naturally occurring glycosides and glycoside conjugates, mataresinol, secoisolariciresinol, enterolactone, enterodiol, textured vegetable protein, and combinations thereof.

Suitable sources of isoflavones for embodiments of this invention include, but are not limited to, soy beans, soy products, legumes, alfalfa sprouts, chickpeas, peanuts, and red clover.

Long-Chain Primary Aliphatic Saturated Alcohol

In certain embodiments, the functional ingredient is at least one long chain primary aliphatic saturated alcohol. Generally, according to particular embodiments of this invention, the at least one long chain primary aliphatic saturated alcohol is present in the edible product, e.g. beverage, in an amount sufficient to promote health and wellness.

Long-chain primary aliphatic saturated alcohols are a diverse group of organic compounds. The term alcohol refers to the fact these compounds feature a hydroxyl group (—OH) bound to a carbon atom. The term primary refers to the fact that in these compounds the carbon atom which is bound to the hydroxyl group is bound to only one other carbon atom. The term saturated refers to the fact that these compounds feature no carbon to carbon pi bonds. The term aliphatic refers to the fact that the carbon atoms in these compounds are joined together in straight or branched chains rather than in rings. The term long-chain refers to the fact that the number of carbon atoms in these compounds is at least 8 carbons).

Non-limiting examples of particular long-chain primary aliphatic saturated alcohols for use in particular embodiments of the invention include the 8 carbon atom 1-octanol, the 9 carbon 1-nonanol, the 10 carbon atom 1-decanol, the 12 carbon atom 1-dodecanol, the 14 carbon atom 1-tetradecanol, the 16 carbon atom 1-hexadecanol, the 18 carbon atom 1-octadecanol, the 20 carbon atom 1-eicosanol, the 22 carbon 1-docosanol, the 24 carbon 1-tetracosanol, the 26 carbon 1-hexacosanol, the 27 carbon 1-heptacosanol, the 28 carbon 1-octanosol, the 29 carbon 1-nonacosanol, the 30 carbon 1-triacontanol, the 32 carbon 1-dotriacontanol, and the 34 carbon 1-tetracontanol.

In a particularly desirable embodiment of the invention, the long-chain primary aliphatic saturated alcohols is policosanol. Policosanol is the term for a mixture of long-chain primary aliphatic saturated alcohols composed primarily of 28 carbon 1-octanosol and 30 carbon 1-triacontanol, as well as other alcohols in lower concentrations such as 22 carbon 1-docosanol, 24 carbon 1-tetracosanol, 26 carbon 1-hexacosanol, 27 carbon 1-heptacosanol, 29 carbon 1-nonacosanol, 32 carbon 1-dotriacontanol, and 34 carbon 1-tetracontanol.

Long-chain primary aliphatic saturated alcohols are derived from natural fats and oils. They may be obtained from these sources by using extraction techniques well known to those of ordinary skill in the art. Policosanols can be isolated from a variety of plants and materials including sugar cane (*Saccharum officinarium*), yams (e.g. *Dioscorea opposite*), bran from rice (e.g. *Oryza sativa*), and beeswax. Policosanols may be obtained from these sources by using extraction techniques well known to those of ordinary skill in the art. A description of such extraction techniques can be found in U.S. Pat. Appl. No. 2005/0220868, the disclosure of which is expressly incorporated by reference.

Phytosterols

In certain embodiments, the functional ingredient is at least one phytosterol, phytostanol or combination thereof. Generally, according to particular embodiments of this invention, the at least one phytosterol, phytostanol or combination thereof is present in the edible product, e.g. beverage, in an amount sufficient to promote health and wellness.

As used herein, the phrases "stanol", "plant stanol" and "phytostanol" are synonymous.

Plant sterols and stanols are present naturally in small quantities in many fruits, vegetables, nuts, seeds, cereals, legumes, vegetable oils, bark of the trees and other plant sources. Although people normally consume plant sterols and stanols every day, the amounts consumed are insufficient to have significant cholesterol-lowering effects or other health benefits. Accordingly, it would be desirable to supplement food and beverages with plant sterols and stanols.

Sterols are a subgroup of steroids with a hydroxyl group at C-3. Generally, phytosterols have a double bond within the steroid nucleus, like cholesterol; however, phytosterols also may comprise a substituted sidechain (R) at C-24, such as an ethyl or methyl group, or an additional double bond. The structures of phytosterols are well known to those of skill in the art.

At least 44 naturally-occurring phytosterols have been discovered, and generally are derived from plants, such as corn, soy, wheat, and wood oils; however, they also may be produced synthetically to form compositions identical to those in nature or having properties similar to those of naturally-occurring phytosterols. According to particular embodiments of this invention, non-limiting examples of phytosterols well known to those or ordinary skill in the art include 4-desmethylsterols (e.g., β-sitosterol, campesterol, stigmasterol, brassicasterol, 22-dehydrobrassicasterol, and Δ5-avenasterol), 4-monomethyl sterols, and 4,4-dimethyl sterols (triterpene alcohols) (e.g., cycloartenol, 24-methylenecycloartanol, and cyclobranol).

As used herein, the phrases "stanol", "plant stanol" and "phytostanol" are synonymous. Phytostanols are saturated sterol alcohols present in only trace amounts in nature and also may be synthetically produced, such as by hydrogenation of phytosterols. According to particular embodiments of this invention, non-limiting examples of phytostanols include β-sitostanol, campestanol, cycloartanol, and saturated forms of other triterpene alcohols.

Both phytosterols and phytostanols, as used herein, include the various isomers such as the α and β isomers (e.g., α-sitosterol and β-sitostanol, which comprise one of the most effective phytosterols and phytostanols, respectively, for lowering serum cholesterol in mammals).

The phytosterols and phytostanols of the present invention also may be in their ester form. Suitable methods for deriving the esters of phytosterols and phytostanols are well known to those of ordinary skill in the art, and are disclosed in U.S. Pat. Nos. 6,589,588, 6,635,774, 6,800,317, and U.S. Patent Publication Number 2003/0045473, the disclosures of which are incorporated herein by reference in their entirety. Non-limiting examples of suitable phytosterol and phytostanol esters include sitosterol acetate, sitosterol oleate, stigmasterol oleate, and their corresponding phytostanol esters. The phytosterols and phytostanols of the present invention also may include their derivatives.

IV. Methods of Use

In one embodiment, the present invention provides a method for modifying the taste (e.g., sweetening the sweetness of) an edible product by administering/consuming the oral dosage form of the present invention prior to consuming the edible product.

The time interval between consumption of the oral dosage form and the edible product may vary. In a particularly embodiment, the time interval is about 1, about 2, about 3, about 4, about 5, about 6, about 7, about 8, about 9 or about 10 minutes or more. In another particular embodiment the time interval is about 10, about 15, about 30, about 45 or about 60 seconds.

As stated previously, oral dosage form of the present invention permits the same or superior sweetness intensity in combination with the same or similar edible product sweetened with a conventional amount of sweetener, e.g., high intensity sweetener. The total carbohydrate intake is therefore lesser, e.g., about 10%, about 15%, about 20%, about 25% or about 30% or less. The edible product itself may or may not contain a sweetener and/or sweetness enhancer.

In a particular embodiment, a method for enhancing the sweetness of a beverage comprising at least one sweetener (e.g., a high intensity sweetener such as rebaudioside M or aspartame) in a concentration above its sweetness recognition threshold is provided, comprising consuming the oral dosage form disclosed prior to consuming the beverage. In exemplary embodiments, the oral dosage form or the oral dosage form plus the edible composition have a reduced carbohydrate total compared to the same or similar beverage sweetened by conventional.

In a particular embodiment, a method for enhancing the sweetness of a beverage not containing an added sweetener or sweetness enhancer is provided, comprising consuming the oral dosage form disclosed herein prior to consuming the beverage. In exemplary embodiments, the oral dosage form or the oral dosage form plus the edible product has a reduced carbohydrate content total compared to the same or similar beverage sweetened by conventional means.

V. Methods of Manufacture

The present invention includes methods of manufacturing the oral dosage forms disclosed herein.

In one embodiment, the oral dosage form is a fast-dissolving tablet and the method of manufacture is selected from freeze drying (lyophilization), tablet molding, spray drying, sublimation, direct compression or nanonization.

In another embodiment, the oral dosage form is a fast-dissolving strip and the method of manufacturing is selected from solvent casting, hot melt extrusion, semi-solvent casting, solid dispersion extrusion and rolling.

In a particular embodiment, the oral dosage form is a fast-dissolving strip and the method of manufacturing is provided in the Examples, below.

In a further embodiment, the oral dosage form is a fast-dissolving capsule and the method of manufacture comprises perforating or vacuum-drying of a conventional hard capsules.

EXAMPLES

Example 1: Film/Strip

| INGREDIENTS | gram |
| --- | --- |
| Water | 67.5 |
| Pectin | 3.5 |
| Fiber-Sol 2 | 20.9375 |
| Miracle fruit Powder | 5.5625 |
| CC00800 (6.25% in PG) | 1.45 |
| Glycerol | 1 |
| Aspartame | 0.05 |
| total | 100 |

Preparation Procedure:

1. Weight and pre-blend all dry ingredients e—Pectin, Fiber-Sol 2, Miracle fruit Powder and Aspartame
2. Weight and pre-blend all wet ingredients—CC00800 (6.25% in PG) and Glycerol
3. Weight the amount of processed water in a container
4. Add pre-blended dry ingredients to the container and mix for ~5 mins
5. Vacuum deaerate the solution if needed.
6 To cast a film, a) pour the pre-blended solution near the edge of a plastic, glass or steel plate. b) Use push bar or film applicator slowly cast a film across the plastic, glass or steel plate
7. Allow the casted film(s) to dry overnight at ambient or in a pre-set temperature oven for a faster drying.
8. After the casted film is dried (5-10% moisture), peel the film off the plate and cut into a size of ~0.04 to 0.3 g for sensory evaluation
1. Sensory Evaluation Examples
2. Sensory Evaluation of Films/Strips Containing Miracle Fruit Pulp/Powder and CC00800, Phloretin and NHDC Sensory evaluations of prepared Miracle Fruit Powder and CC00800 films/strips were completed in various beverages listed below. There are 12 participants. Different doses (from 0.04 g to 1.0 g) of films/strips were served and held in the mouth/tongue for ~15 seconds or longer. The beverages evaluated and sensory comments are listed below.

Beverage Samples

| Beverage | Evaluation Comments |
| --- | --- |
| Citrus buffer solution with 5% Sucrose | Improve sweetness intensity for strip weight >~0.04 g or higher (higher the doses the more intense the sweetness). Panelist feel 5% sucrose solution taste like 8-12 brix sweet equivalence (SE) |
| Citrus buffer solution with 120 ppm Rebaudioside M | Improve sweetness profile (sugar like), and significantly reduced bitterness after taste and intensity for strip weight 0.04 g or higher (higher the doses the more intense the sweetness/sugar like profile) Panelist feel 5% sucrose solution taste like 8-12 brix SE |
| Cola flavor beverage with 5% sucrose | Improve sweetness intensity to ~7-10 Brix SE for strip weight ~0.08 g or higher (higher the doses the more intense the sweetness) |
| Cola flavor beverage with 7% sucrose - carbonated to 4 vol. $CO_2$ | Improve sweetness intensity to ~8-11 Brix for strip weight >~0.06 g or higher (higher the doses the more intense the sweetness) |
| reduced calories mixed juice | Improve sweetness profile (sugar like) and intensity for strip weight 0.04 g or higher (higher the doses the more intense - 9-11 brix SE (from 5 brix SE) the sweetness/sugar like profile |
| Berry flavor Vitaminwater Zero cal. | Improve sweetness profile (sugar like)/intensity and reduce bitterness after taste from Stevia sweetened beverage for strip weight >~0.04 g or higher (higher the doses the more intense the sweetness/sugar like profile), the sweetness increase from 6-7 brix SE to 10-12 Brix SE |
| Orange juice | Improve sweetness intensity to ~12+ Brix SE for strip weight 0.04 g or higher (higher the doses the more intense the sweetness) |
| Lemonade | Improve sweetness intensity to ~12+ Brix SE for strip weight >~0.04 g or higher (higher the doses the more intense the sweetness) |
| 1 part of Lemonade + 1 part of process water | Improve sweetness intensity from 6 brix SE to ~9-12 Brix SE for strip weight >~0.04 g or higher (higher the doses the more intense the sweetness) |

Example 2

A dissolvable strip is prepared comprising the ingredients shown in Table 2, below:

TABLE 2

| Ingredient | Grams |
| --- | --- |
| Water | 69.465 |
| Pectin | 2.0 |
| Pullulan | 15.0 |
| Miracle fruit powder | 10.0 |
| Phloretin in PG (6.25%) | 3.0 |
| Glycerol | 0.5 |
| Reb M | 0.035 |
| Total | 100 |

Preparation Procedure:

1. Weigh and pre-blend all dry ingredients—Pectin, Pullulan, Miracle fruit Powder and Aspartame
2. Weigh and pre-blend all wet ingredients—Phloretin (6.25% in PG) and Glycerol
3. Weigh the amount of processed water in a container 4. Add pre-blended dry ingredients to the container and mix for ~5 mins 5. Vacuum deaerate the solution if needed.

6. To cast a film, a) pour the pre-blended solution near the edge of a plastic, glass or steel plate. b) use push bar or film applicator slowly cast a film across the plastic, glass or steel plate 7. Allow the casted film(s) to dry overnight at ambient or in a pre-set temperature oven for a faster drying.

8. After the casted film is dried (5-10% moisture), peel the film off the plate and cut into a size of ~0.04 to 0.3 g for sensory evaluation Example 3

A dissolvable strip is prepared comprising the ingredients shown in Table 3, below:

TABLE 3

| Ingredient | Grams |
| --- | --- |
| Water | 71.515 |
| Pectin | 2.0 |
| Pullulan | 18.0 |
| Miracle fruit powder | 7.0 |
| Phloretin in PG | 1.45 |
| Glycerol | 0.5 |
| Reb M | 0.035 |
| Total | 100 |

Preparation Procedure:

1. Weigh and pre-blend all dry ingredients—Pectin, Pullulan, Miracle fruit Powder and Reb M 2. Weigh and pre-blend all wet ingredients—Phloretin (6.25% in PG) and Glycerol 3. Weigh the amount of processed water in a container 4. Add pre-blended dry ingredients to the container and mix for ~5 mins 5. Vacuum deaerate the solution if needed.

6. To cast a film, a) pour the pre-blended solution near the edge of a plastic, glass or steel plate. b) use push bar or film applicator slowly cast a film across the plastic, glass or steel plate 7. Allow the casted film(s) to dry overnight at ambient or in a pre-set temperature oven for a faster drying.

8. After the casted film is dried (5-10% moisture), peel the film off the plate and cut into a size of ~0.04 to 0.3 g for sensory evaluation Example 4

A dissolvable strip is prepared comprising the ingredients shown in Table 4, below:

TABLE 4

| Ingredient | Grams |
| --- | --- |
| Water | 72.25 |
| Xanthan | 0.15 |
| Locust bean gum | 0.15 |
| Pullulan | 18.0 |
| Miracle fruit powder | 7.0 |
| NHDC in PG (5%) | 1.45 |
| Glycerol | 0.5 |
| Total | 100 |

Preparation Procedure:

1. Weigh and pre-blend all dry ingredients—Xanthan, Locust bean gum, Pullulan, Miracle fruit Powder 2. Weigh and pre-blend all wet ingredients—NHDC (6.25% in PG) and Glycerol 3. Weigh the amount of processed water in a container 4. Add pre-blended dry ingredients to the container and mix for ~5 mins 5. Vacuum deaerate the solution if needed.

6. To cast a film, a) pour the pre-blended solution near the edge of a plastic, glass or steel plate. b) use push bar or film applicator slowly cast a film across the plastic, glass or steel plate 7. Allow the casted film(s) to dry overnight at ambient or in a pre-set temperature oven for a faster drying.

8. After the casted film is dried (5-10% moisture), peel the film off the plate and cut into a size of ~0.04 to 0.3 g for sensory evaluation Example 5

A dissolvable strip is prepared comprising the ingredients shown in Table 5, below.

TABLE 5

| Ingredient | Grams |
| --- | --- |
| Water | 68.75 |
| Xanthan | 0.15 |
| Locust bean gum | 0.15 |
| Pullulan | 18.0 |
| Miracle fruit powder | 7.0 |
| Orange flavor | 4.0 |
| NHDC in PG (5%) | 1.45 |
| Glycerol | 0.5 |
| Total | 100 |

Preparation Procedure:

1. Weigh and pre-blend all dry ingredients—Xanthan, Locust bean gum, Pullulan, Miracle fruit Powder 2. Weigh and pre-blend all wet ingredients—NHDC (5% in PG), Glycerol and Orange flavor 3. Weigh the amount of processed water in a container 4. Add pre-blended dry ingredients to the container and mix for ~5 mins 5. Vacuum deaerate the solution if needed.

6. To cast a film, a) pour the pre-blended solution near the edge of a plastic, glass or steel plate. b) use push bar or film applicator slowly cast a film across the plastic, glass or steel plate 7. Allow the casted film(s) to dry overnight at ambient or in a pre-set temperature oven for a faster drying.

8. After the casted film is dried (5-10% moisture), peel the film off the plate and cut into a size of ~0.04 to 0.3 g for sensory evaluation.

Example 6

A dissolvable strip is prepared comprising the ingredients shown in Table 6, below.

TABLE 6

| Ingredient | Grams |
| --- | --- |
| Miracle Fruit Pulp | 80 |
| Pectin | 3.2 |
| Fiber-Sol 2 | 14.5 |

TABLE 6-continued

| Ingredient | Grams |
| --- | --- |
| hesperetin dihydrochalcone (6.25% in PG) | 1.4 |
| Glycerol | 0.9 |
| Total | 100 |

Preparation Procedure:

1. Weigh and de-freeze miracle fruit pulp in a container
2. Weigh and pre-blend all dry ingredients—Pectin, Fiber-Sol 2
3. Weigh and pre-blend all wet ingredients—hesperetin dihydrochalcone (6.25% in PG) and Glycerol
4. Add pre-blended dry ingredients to the container and mix for ~5 mins
5. Vacuum deaerate the solution if needed
6. To cast a film, a) pour the pre-blended solution near the edge of a plastic, glass or steel plate. b) Use push bar or film applicator slowly cast a film across the plastic, glass or steel plate
7. Allow the casted film(s) to dry overnight at ambient or in a pre-set temperature oven for a faster drying
8. After the casted film is dried (~5-10% moisture), peel the film off the plate and cut into a size of ~0.04 to 0.3 g for sensory evaluation Example 7: Edible Gel or Edible Gel Mix

| INGREDIENTS | grams |
| --- | --- |
| Water | 75 |
| Pectin | 2.5 |
| Fiber-Sol 2 | 15 |
| Miracle fruit Powder | 6 |
| hesperetin dihydrochalcone (6.25% in PG) | 1.46 |
| Reb M | 0.04 |
| total | 100 |

Preparation Procedure:

1. Weight and pre-blend all dry ingredients—Pectin, Fiber-Sol 2, Miracle fruit Powder and Reb M
2. Weight and pre-blend all wet ingredients—hesperetin dihydrochalcone (6.25% in PG)
3. Weight the amount of processed water in a container
4. Add pre-blended dry ingredients to the container and mix for ~5 mins
5. Vacuum deaerate the solution if needed.
6. Prepare ~0.1 g to 2.0 g of the edible gel in a weighting pan for sensory evaluation Example 8: Edible Liquid Concentrate or Drop

| INGREDIENTS | grams |
| --- | --- |
| Water | 87.12 |
| Potassium Sorbate | 0.08 |
| Pectin | 0.2 |
| Xanthan gum | 0.1 |
| Fiber-Sol 2 | 5 |
| Miracle fruit Powder | 6 |
| HESPERETIN DIHYDROCHALCONE (6.25% in PG) | 1.46 |
| Reb M | 0.04 |
| total | 100 |

Preparation Procedure:

1. Weight and pre-blend all dry ingredients—Pectin, Fiber-Sol 2, Miracle fruit Powder and Reb M
2. Weight the wet ingredient—HESPERETIN DIHYDROCHALCONE (6.25% in PG)
3. Weight the amount of processed water in a container
4. Add potassium sorbate to the container and mix for 3-5 mins
4. Add pre-blended dry ingredients to the container and mix for ~5 mins
5. Homogenize the solution by high pressure homogenizer at 3000 psi (2500 psi+500 psi) 5. Vacuum deaerate the solution if needed.
6. Prepare ~0.05 g to 2.0 g of the edible liquid concentrate/drop in a weighting pan for sensory evaluation Example 9: Dry Powder Mix (can Also be Made into Tablet or Gel Capsule)

| INGREDIENTS | grams |
| --- | --- |
| Pectin | 1 |
| Fiber-Sol 2 | 50 |
| Miracle fruit Powder | 48.8 |
| Phloretin | 0.15 |
| Reb M | 0.05 |
| total | 100 |

Preparation Procedure:

1. Weight and pre-blend all dry ingredients—Pectin, Fiber-Sol 2, Miracle fruit Powder, Phloretin and Reb M
2. Prepare ~0.02 g to 0.5 g of dry powder mix in a weighting pan for sensory evaluation Example 10: Film/Strip—Miracle Fruit Powder Only

| INGREDIENTS | gram |
| --- | --- |
| Water | 68.5 |
| Pectin | 3.5 |
| Fiber-Sol 2 | 18 |
| Miracle fruit Powder | 8 |
| Propylene Glycol | 1 |
| Glycerol | 1 |
| total | 100 |

Preparation Procedure:

1. Weight and pre-blend all dry ingredients e—Pectin, Fiber-Sol 2 and Miracle fruit Powder
2. Weight and pre-blend all wet ingredients—Propylene Glycol and Glycerol
3. Weight the amount of processed water in a container 4. Add pre-blended dry ingredients to the container and mix for ~5 mins 5. Vacuum deaerate the solution if needed.

6 To cast a film, a) pour the pre-blended solution near the edge of a plastic, glass or steel plate. b) Use push bar or film applicator slowly cast a film across the plastic, glass or steel plate 7. Allow the casted film(s) to dry overnight at ambient or in a pre-set temperature oven for a faster drying.

8. After the casted film is dried (5-10% moisture), peel the film off the plate and cut into a size of ~0.04 to 0.3 g for sensory evaluation 3. Sensory Evaluation Examples 4. Sensory Evaluation of Films/Strips Containing Miracle Fruit Pulp/Powder Sensory evaluations of prepared Miracle Fruit Powder films/strips were completed in various beverages listed below. There are 12 participants. Different doses (from 0.04 g to 1.0 g) of films/strips were served and held in the mouth/tongue for ~15 seconds or longer. The beverages evaluated and sensory comments are listed below.

Beverage Samples

| Beverage | Evaluation Comments |
|---|---|
| Citrus buffer solution with 5% Sucrose | Improve sweetness intensity for strip weight >~0.04 g or higher (higher the doses the more intense the sweetness) Panelist feel 5% sucrose solution taste like 6-9 brix sweet equivalence (SE), but feel less mouth feel vs. 6-9 birx sugar solution |
| Citrus buffer solution with 120 ppm Rebaudioside M | Improve sweetness intensity, but not sugar like and intensity for strip weight >~0.04 g or higher (higher the doses the more intense the sweetness/sugar like profile), Panelist feel 5% sucrose solution taste like 6-10 brix SE, with pretty strong bitter, metallic after taste, and no sugar like mouthfeel |
| Cola flavor beverage with 5% sucrose | Improve sweetness intensity to ~6 Brix for strip weight >~0.08 g or higher (higher the doses the slightly more intense the sweetness), not effective for phosphoric acid based beverages |
| Cola flavor beverage with 7% sucrose—carbonated to 4 vol. CO2 | Improve sweetness intensity to ~7-8 Brix for strip weight >~0.08 g or higher (higher the doses the slightly more intense the sweetness), not effective for phosphoric acid based beverages |
| reduced calories mixed juice | Increase sweetness intensity for strip weight >~0.06 g or higher (higher the doses the more intense the sweetness, but no sugar like mouthfeel) |
| Berry flavor Vitaminwater Zero cal. | Increase sweetness intensity, but not sugar like sweetness profile for strip weight >~0.06 g or higher (higher the doses the more intense the sweetness, but not sugar like profile), panelist feel the sweetness increase to 7-9 SE, but with strong metallic and bitter after taste |
| Orange juice | Improve sweetness intensity to ~11 Brix for strip weight >~0.06 g or higher (higher the doses the more intense the sweetness) |
| Lemonade | Improve sweetness intensity to ~12+ Brix for strip weight >~0.06 g or higher (higher the doses the more intense the sweetness) |
| 1 part of Lemonade + 1 part of process water | Improve sweetness intensity to ~7-8 Brix for strip weight >~0.06 g or higher (higher the doses the more intense the sweetness), but the taste is much diluted on mouthfeel |

Example 11: Dough for Pills and Paste (to Prepare and Compress to Different Shapes)

| INGREDIENTS | grams |
|---|---|
| Pectin | 5 |
| Fiber-Sol 2 | 40 |
| Miracle fruit Powder | 40 |
| CC00800 in propylene glycol (6.25%) | 1.5 |
| Glycerol | 13.5 |
| total | 100 |

Preparation Procedure:

1. Weight and pre-blend all dry ingredients (except 1 gram of Fiber-Sol 2)—Pectin, Fiber-Sol 2, Miracle fruit Powder 2. Weight and pre-blend all wet ingredients—CC00800 in Propylene Glycol and Glycerol 3. Blend the dry blend (except 1 gram of Fiber-Sol 2) with the wet blend using a dough blender for ~15 mins 4. Prepare small pieces of 0.02 g to 0.5 g of the blended dough and dust the Fiber-Sol 2 powder to prevent caking 5. Prepare small pieces of 0.02 g to 0.5 g in a weighting pan for sensory evaluation Example 12: Production of Fruit Bits or Fruit Pieces

| Ingredient | 100 g |
|---|---|
| Water | 2 |
| Pullulan | 37.8 |
| Miracle Fruit Powder | 30 |
| Glycerin | 30 |
| Rebaudioside A (Reb A) | 0.2 |
| Total weight, g | 100 |

The dry ingredients are pre-blended as uniform powder blend. The liquid ingredients are pre-mixed as uniform mixture. The liquid mixture is slowly added to the dry powder blend to make a dough. The dough is then stored at ambient or at elevated temperature such as 35 C for extended period of time (upto 5 days). The aged dough is pressed to form about 1-2 mm thick fruit sheet and cut into fruit pieces (e.g., 2 mm×1 cm×1 cm) or bits (e.g., 2 mm×2 mm×2 mm). The fruit pieces and fruit bits can be consumed by itself or blended with other ingredients such as carbonated crystal.

Example 13: Production of Fruit Bits or Fruit Pieces

| Ingredient | 100 g |
|---|---|
| Pullulan | 42.5 |
| Miracle Fruit Powder | 42.5 |
| Glycerin | 14.9 |
| Reb A | 0.1 |
| Total weight, g | 100 |

The dry ingredients are pre-blended as uniform powder blend. The liquid ingredients are pre-mixed as uniform mixture. The liquid mixture is slowly added to the dry powder blend to make a dough. The dough is then stored at ambient for extended period of time (upto 1-2 days). The dough is pressed to form about 1-2 mm thick fruit sheet and cut into fruit pieces (e.g., 2 mm×1 cm×1 cm) or bits (e.g., 2 mm×2 mm×2 mm). The fruit pieces and fruit bits can be consumed by itself or blended with other ingredients such as carbonated crystal.

Example 14: Fruit Bits and Carbonated Crystal

| Ingredient | 100 g |
| --- | --- |
| Pullulan | 16.5 |
| Miracle Fruit Powder | 15 |
| Glycerin | 15.9 |
| Reb A | 0.1 |
| Tapioca starch | 2.5 |
| Isomalt carbonated crystal | 50 |
| Total weight, g | 100 |

0.5 g of the fruit bits (e.g., 2 mm×2 mm×2 mm) and 0.5 g isomalt carbonated crystal are then blended and packaged into a moisture barrier pouch for consumption.

Example 15: Fruit Bits and Carbonated Crystal

| Ingredient | 100 g |
| --- | --- |
| Pullulan | 17 |
| Miracle Fruit Powder | 17 |
| Glycerin | 5.96 |
| Reb A | 0.04 |
| Isomalt carbonated crystal | 60 |
| Total weight, g | 100 |

0.4 g of the fruit bits (e.g., 2 mm×2 mm×2 mm) and 0.6 g isomalt carbonated crystal are then blended and packaged into a moisture barrier pouch for consumption.

The invention claimed is:

1. A film comprising miraculin and at least one dihydrochalcone derivative selected from the group consisting of hesperetin dihydrochalcone, phloretin, neohesperidin dihydrochalcone, naringin dihydrochalcone and combinations thereof, wherein the miraculin and the at least one dihydrochalcone derivative are present in a ratio of from about 500:1 or less, and wherein the film dissolves within the oral cavity in less than about 3 minutes.

2. The film of claim 1, wherein the miraculin and the at least one dihydrochalcone derivative are present in a ratio of from about 100:1 or less.

3. The film of claim 1, wherein the miraculin and the at least one dihydrochalcone derivative are present in a ratio of from about 10:1 or less.

4. The film of claim 1, wherein the miraculin is provided as miracle fruit powder.

5. The film of claim 4, wherein the amount of miraculin in the miraculin fruit powder is from about 0.01 to about 1 wt. %.

6. The film of claim 1, further comprising at least one high intensity sweetener, at least one sweetness enhancer or combinations thereof.

7. The film of claim 1, further comprising at least one high intensity sweetener, wherein the at least one high intensity sweetener is natural.

8. The film of claim 7, wherein the at least one natural one high intensity sweetener is rebaudioside M having a purity of from about 80% to about 100%.

9. The film of claim 7, wherein the at least one natural one high intensity sweetener is rebaudioside A.

10. The film of claim 1, further comprising at least one high intensity sweetener, wherein the at least one high intensity sweetener is synthetic.

11. The film of claim 9, wherein the at least one synthetic high intensity sweetener is aspartame.

12. The film of claim 1, further comprising at least one excipient selected from a water-soluble polymer, a plasticizer and a saliva-inducing agent.

13. A method for enhancing the sweetness of an edible product, comprising consuming the film of claim 1 prior to consuming the edible product.

14. The method of claim 13, wherein the edible product is a beverage or beverage product.

15. The method of claim 13, wherein the edible product is a reduced or non-calorie beverage.

16. The method of claim 13, wherein the film is consumed less than 3 minutes before consuming the edible product.

17. The method of claim 13, wherein the film provides between about 5 to about 10 brix sweetness at a reduced concentration of carbohydrates compared to conventionally sweetened edible products.

18. The method of claim 17, wherein the concentration of carbohydrates is reduced by about 10% or more.

* * * * *